(12) United States Patent
Reitz et al.

(10) Patent No.: US 7,534,348 B2
(45) Date of Patent: May 19, 2009

(54) FLOW-THROUGH REMOVAL DEVICE AND SYSTEM USING SUCH DEVICE

(75) Inventors: Douglas W. Reitz, Green Oaks, IL (US); Scott Ariagno, Mundelein, IL (US); Mihir Sheth, Gurnee, IL (US); Atif Yardimci, Northbrook, IL (US); Robert A. Clarke, Libertyville, IL (US); David W. Pennington, Fox Lake, IL (US); Michael R. Prisco, Geneva, IL (US); Edwin Chim, Vernon Hills, IL (US); Robin Pauley, Lake Villa, IL (US); Craig Sandford, Buffalo Grove, IL (US); Arch Sites, Woodstock, IL (US)

(73) Assignee: Fenwal, Inc., Lake Zurich, IL (US)

( * ) Notice: Subject to any disclaimer, the term of this patent is extended or adjusted under 35 U.S.C. 154(b) by 70 days.

(21) Appl. No.: 10/661,994

(22) Filed: Sep. 12, 2003

(65) Prior Publication Data

US 2005/0056580 A1 Mar. 17, 2005

(51) Int. Cl.
*B01D 29/00* (2006.01)
*B01D 37/00* (2006.01)
*A61M 5/165* (2006.01)

(52) U.S. Cl. .................. 210/232; 210/445; 210/446; 210/483

(58) Field of Classification Search .......... 210/232, 210/445, 446, 483
See application file for complete search history.

(56) References Cited

U.S. PATENT DOCUMENTS

| | | | |
|---|---|---|---|
| 3,864,265 A * | 2/1975 | Markley | 210/321.77 |
| 3,905,905 A * | 9/1975 | O'Leary et al. | 210/436 |
| 3,932,153 A | 1/1976 | Byrns et al. | |
| 4,009,714 A | 3/1977 | Hammer et al. | |
| 4,157,967 A | 6/1979 | Meyst et al. | |
| 4,163,721 A * | 8/1979 | Lobdell | 210/232 |
| 4,170,056 A | 10/1979 | Meyst et al. | |
| 4,326,957 A * | 4/1982 | Rosenberg | 210/436 |
| 4,453,927 A * | 6/1984 | Sinko | 604/513 |
| 5,147,545 A | 9/1992 | Despard et al. | |

(Continued)

FOREIGN PATENT DOCUMENTS

EP 0 313 348 4/1989

(Continued)

OTHER PUBLICATIONS

Aricle entitled "Designing Parts for Ultrasonic Welding," 1980, Branson Ultrasonics Corporation, Danbury, Connecticut.

(Continued)

*Primary Examiner*—Thomas M Lithgow
(74) *Attorney, Agent, or Firm*—Cook Alex Ltd.

(57) ABSTRACT

Flow-through systems for processing biological fluid are disclosed. The flow-through systems include a removal device in the flow path for removing unwanted compounds and agents. The removal device includes a removal media contained within a housing made of two separate portions sealed together. The housing is maintained in a substantially vertical disposition, thereby ensuring substantially uniform and complete exposure of the fluid to the media.

17 Claims, 19 Drawing Sheets

U.S. PATENT DOCUMENTS

| | | | |
|---|---|---|---|
| 5,269,917 A * | 12/1993 | Stankowski | 210/232 |
| 5,451,321 A | 9/1995 | Matkovich | |
| 5,458,719 A * | 10/1995 | Pall et al. | 156/285 |
| 5,472,621 A | 12/1995 | Matkovich et al. | |
| 5,501,795 A * | 3/1996 | Pall et al. | 210/508 |
| 5,601,730 A | 2/1997 | Page et al. | |
| 5,660,731 A | 8/1997 | Piechocki et al. | |
| 5,853,587 A | 12/1998 | Young et al. | |
| 5,938,940 A * | 8/1999 | Zuk, Jr. | 210/767 |
| 5,975,312 A | 11/1999 | Bonsan et al. | |
| 6,010,633 A * | 1/2000 | Zuk et al. | 210/767 |
| 6,051,136 A | 4/2000 | Mari | |
| 6,086,762 A * | 7/2000 | Guala | 210/232 |
| 6,143,174 A | 11/2000 | Graus | |
| 6,159,377 A | 12/2000 | Davankov et al. | |
| 6,168,653 B1 * | 1/2001 | Myers | 96/4 |
| 6,251,292 B1 | 6/2001 | Zuk, Jr. | |
| 6,337,026 B1 | 1/2002 | Lee et al. | |
| 6,358,420 B2 | 3/2002 | Blickhan et al. | |
| 6,364,864 B1 * | 4/2002 | Mohiuddin et al. | 604/410 |
| 6,488,860 B2 | 12/2002 | Mari et al. | |
| 7,060,183 B1 * | 6/2006 | Goudaliez et al. | 210/232 |
| 2001/0009756 A1 * | 7/2001 | Hei et al. | 435/2 |
| 2002/0148765 A1 | 10/2002 | Zia et al. | |
| 2003/0146162 A1 | 8/2003 | Metzel et al. | |

FOREIGN PATENT DOCUMENTS

| | | | |
|---|---|---|---|
| EP | 0 563 581 | | 10/1993 |
| EP | 0 773 051 A1 | | 5/1997 |
| EP | 1106192 | * | 6/2001 |
| GB | 978065 | | 11/1962 |
| GB | 2 266 477 A | | 11/1993 |

OTHER PUBLICATIONS

Brochure entitled "Plastics Assembly News," Sep. 1989, Branson Ultrasonics Corporation, Danbury, Connecticut.

International Search Report re application No. PCT/US2004/029637, dated Jun. 17, 2005.

Written Opinion re application No. PCT/US2004/029637, dated Jun. 17, 2005.

EPO Application No. 04 816 859.5-2113 - Examination Report dated Jul. 1, 2008.

* cited by examiner

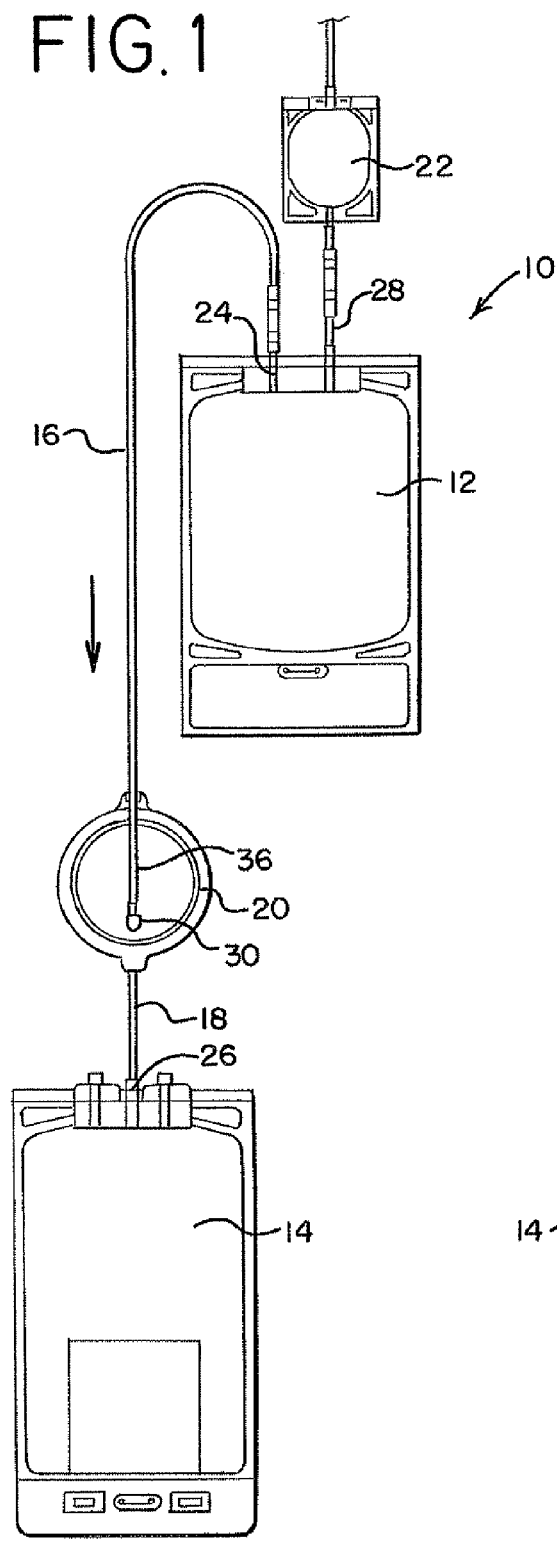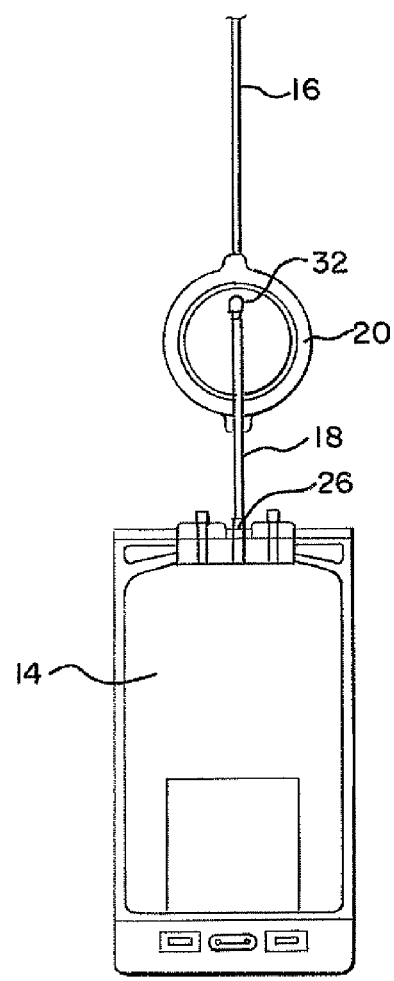

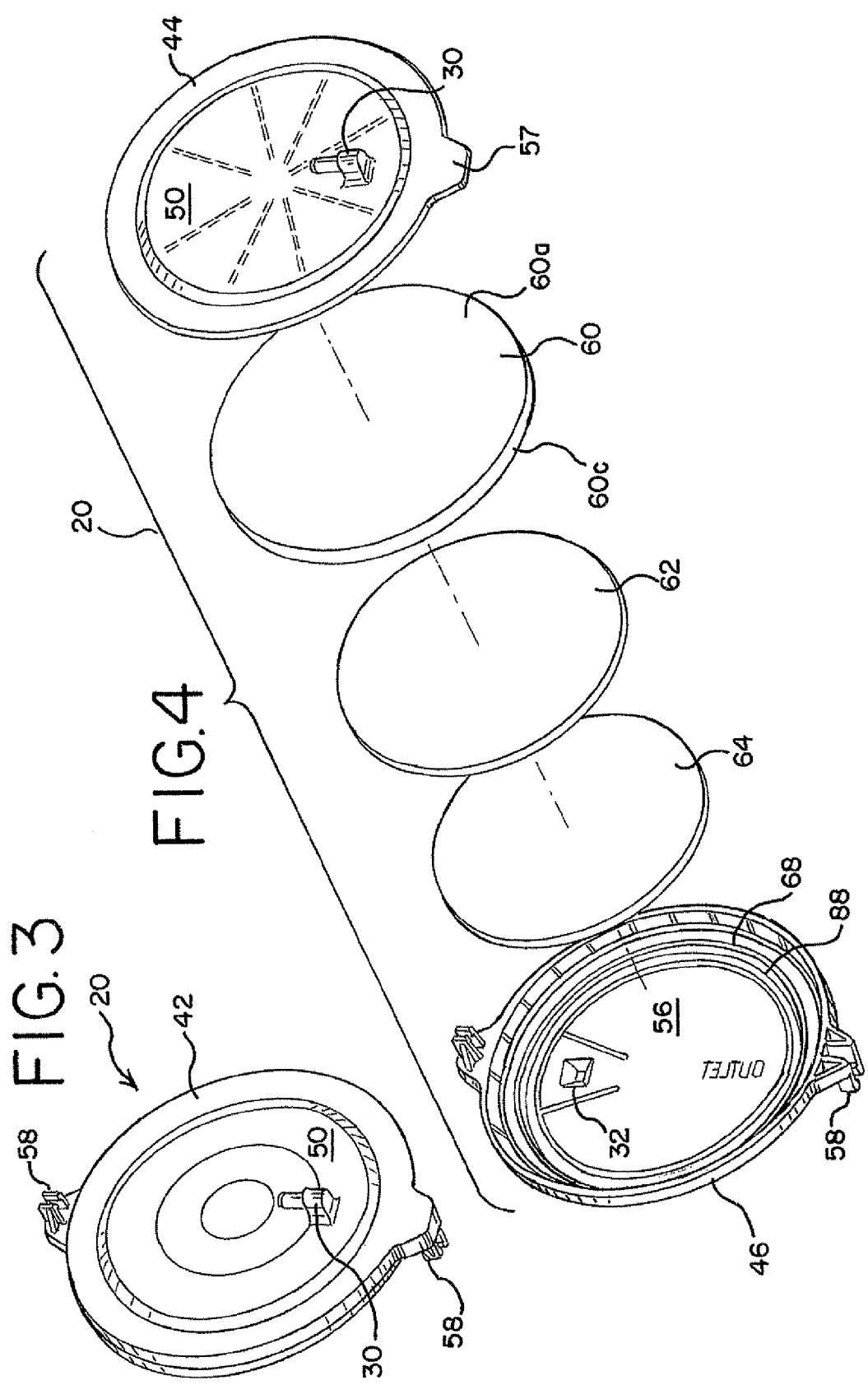

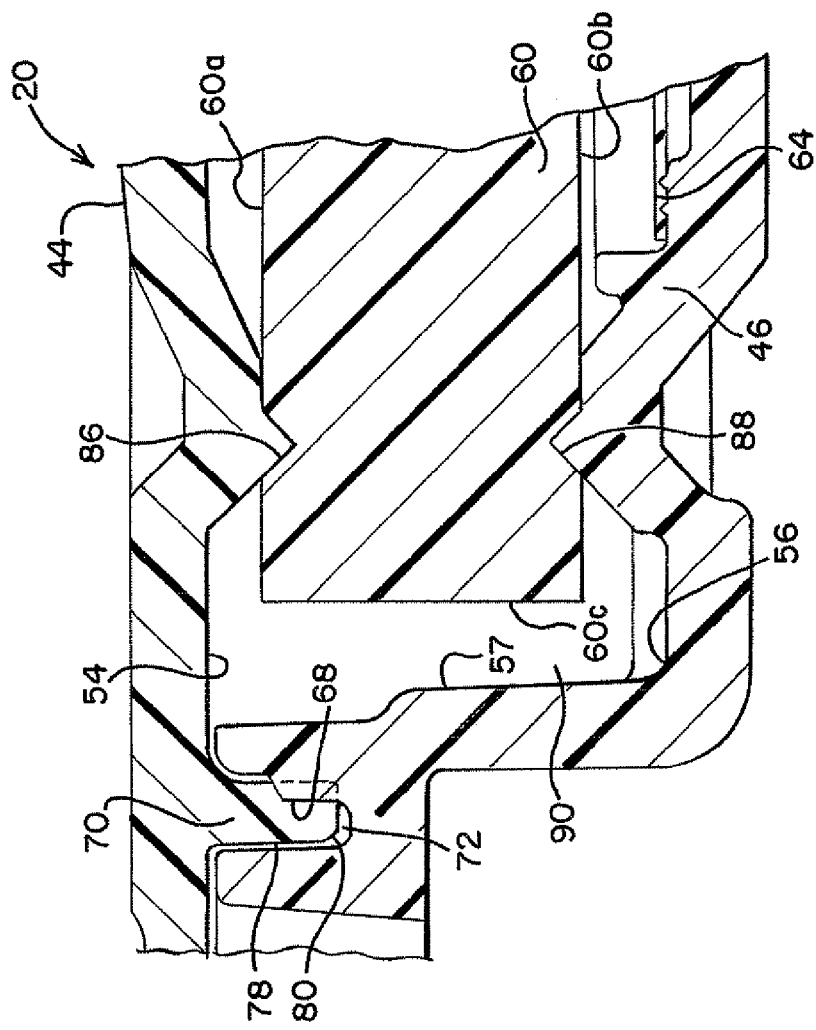
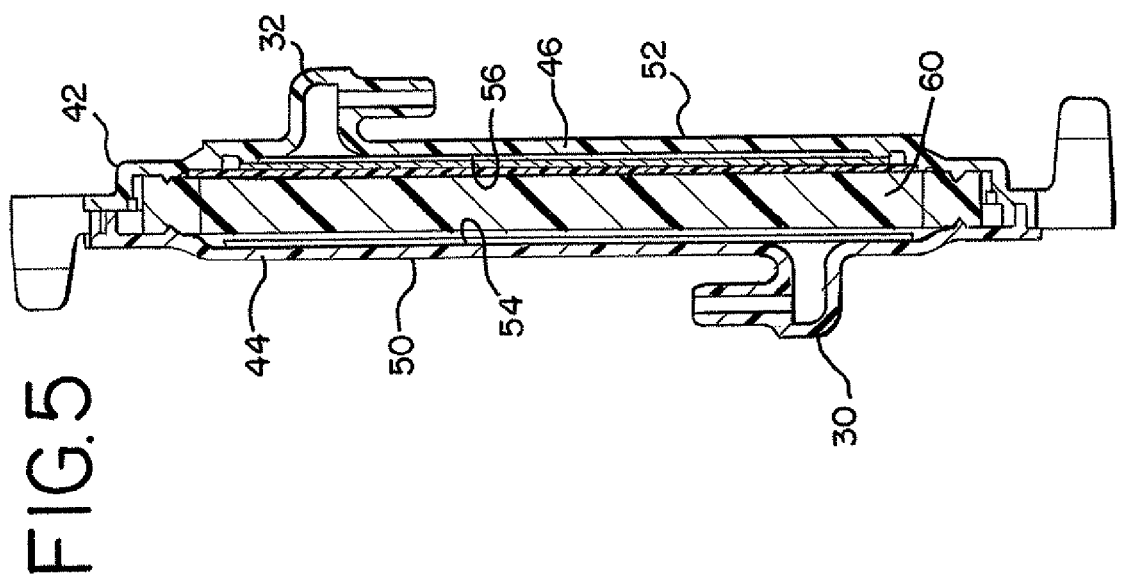

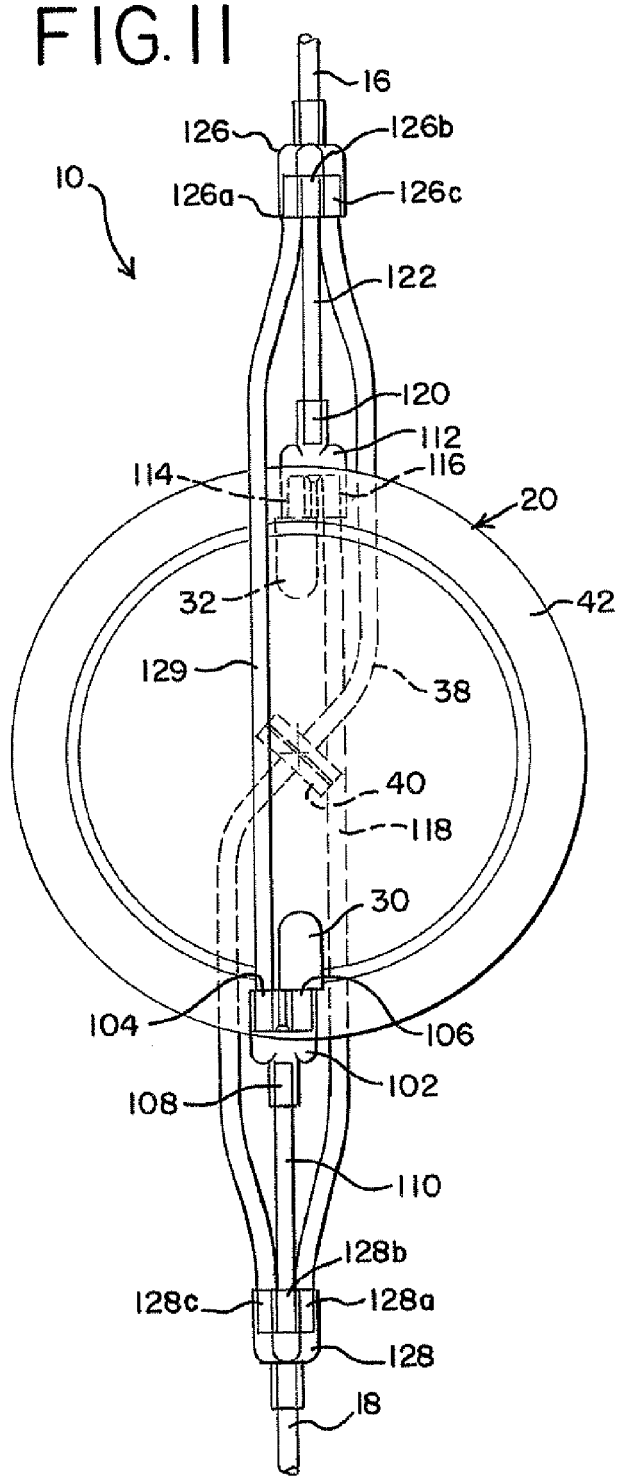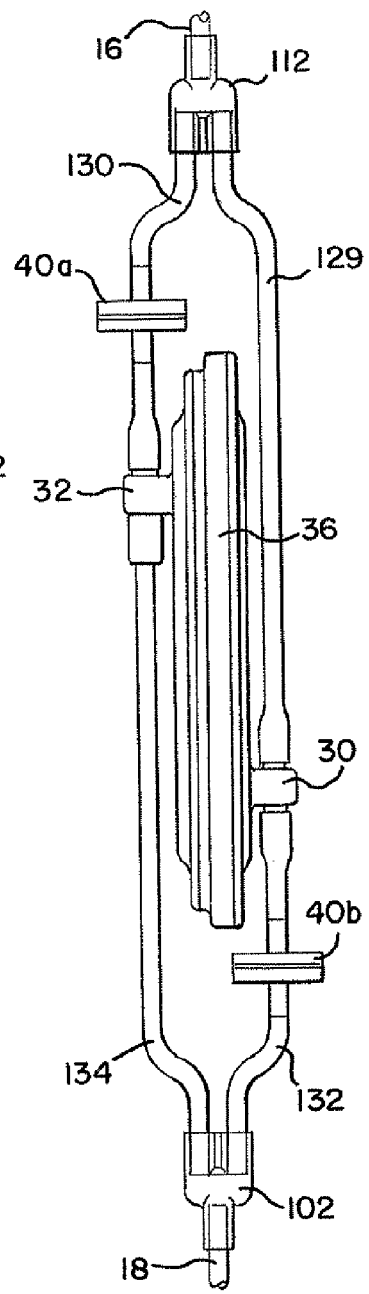

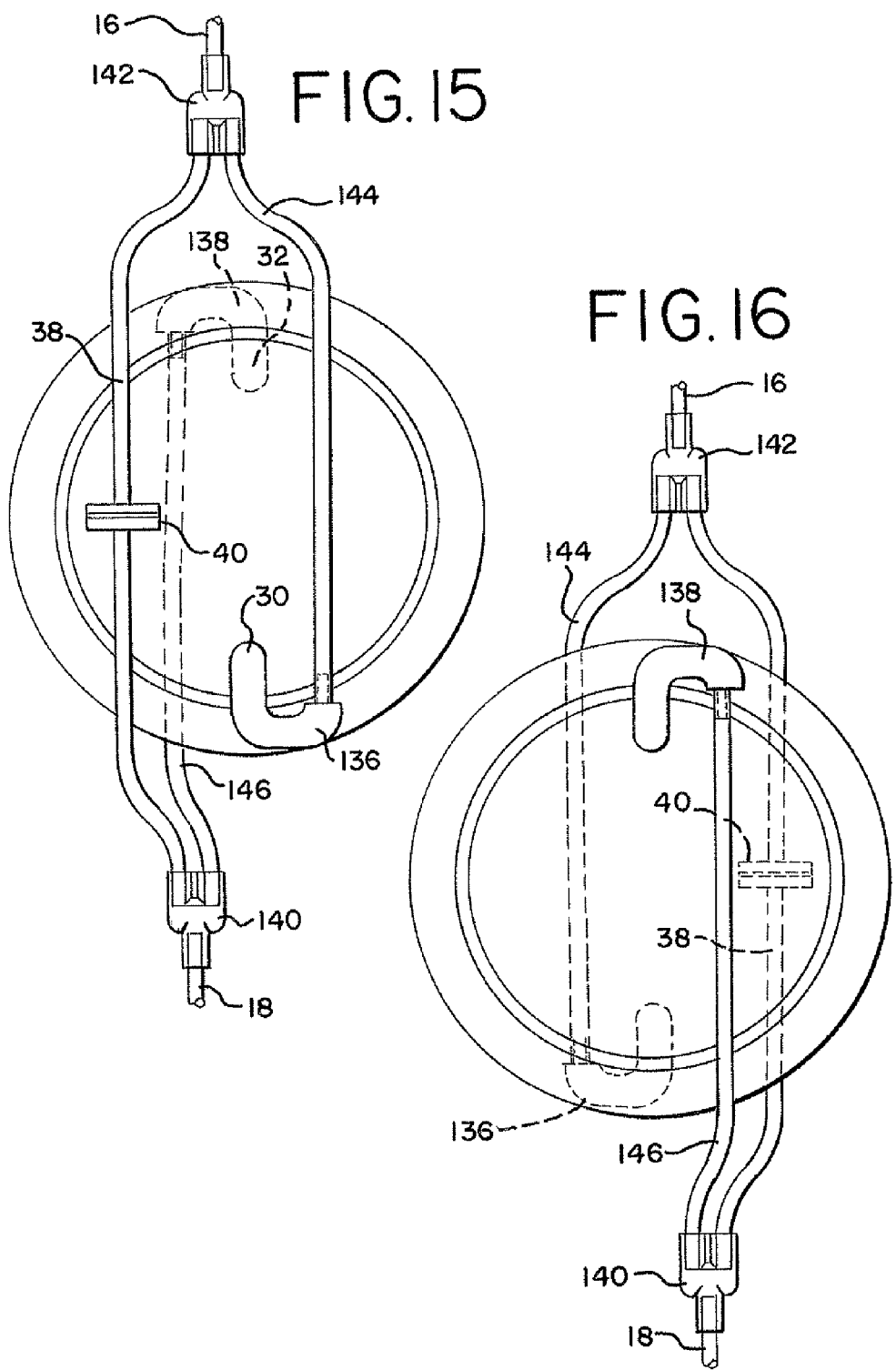

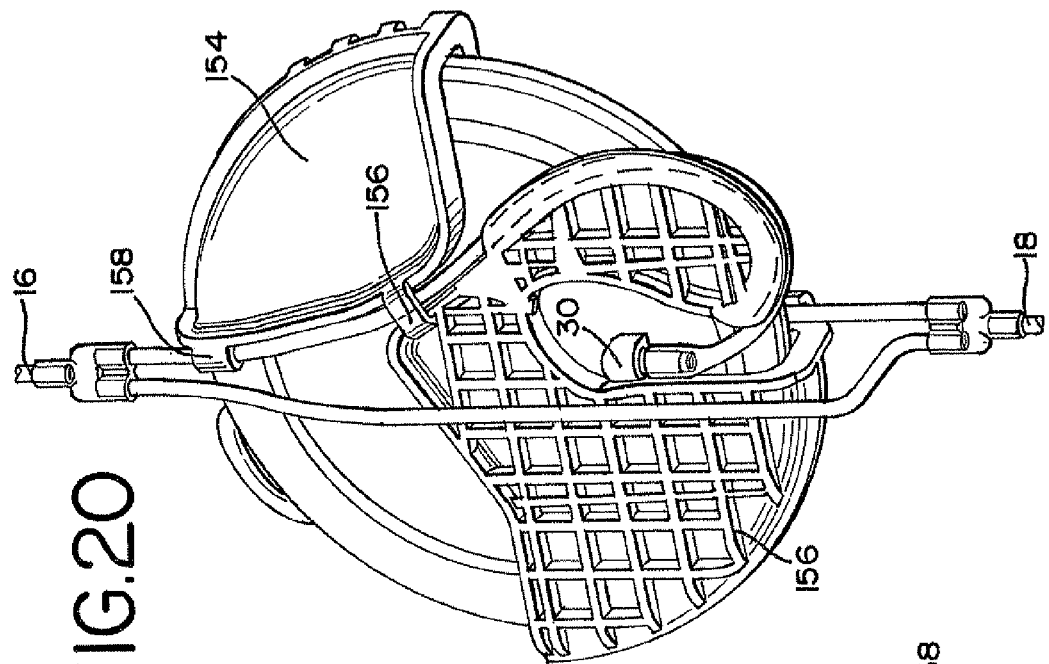
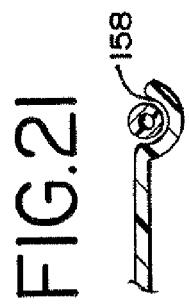
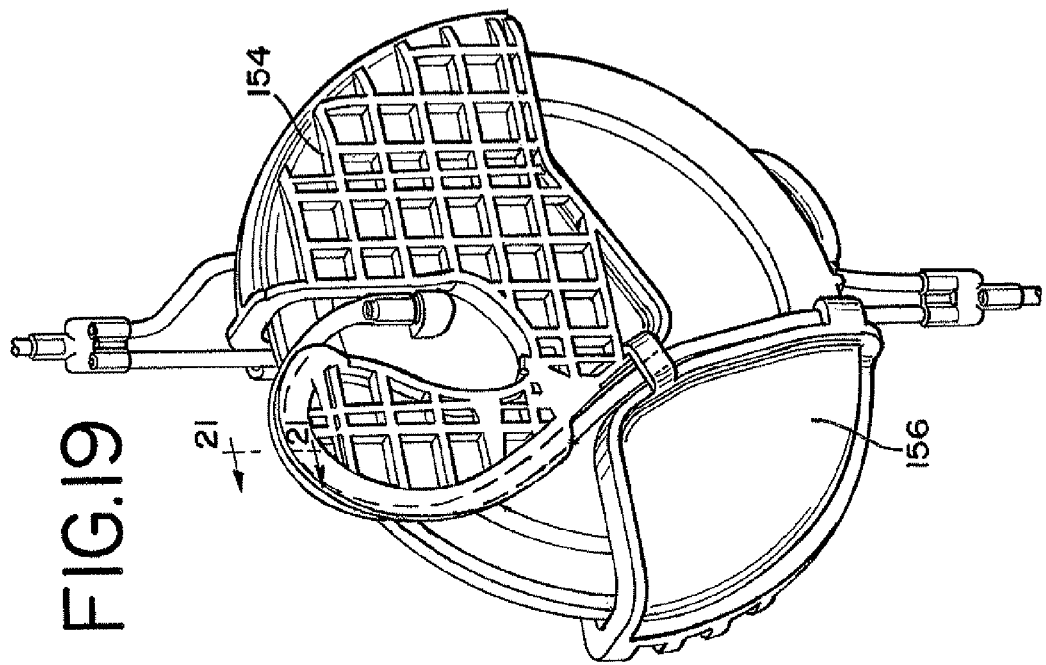

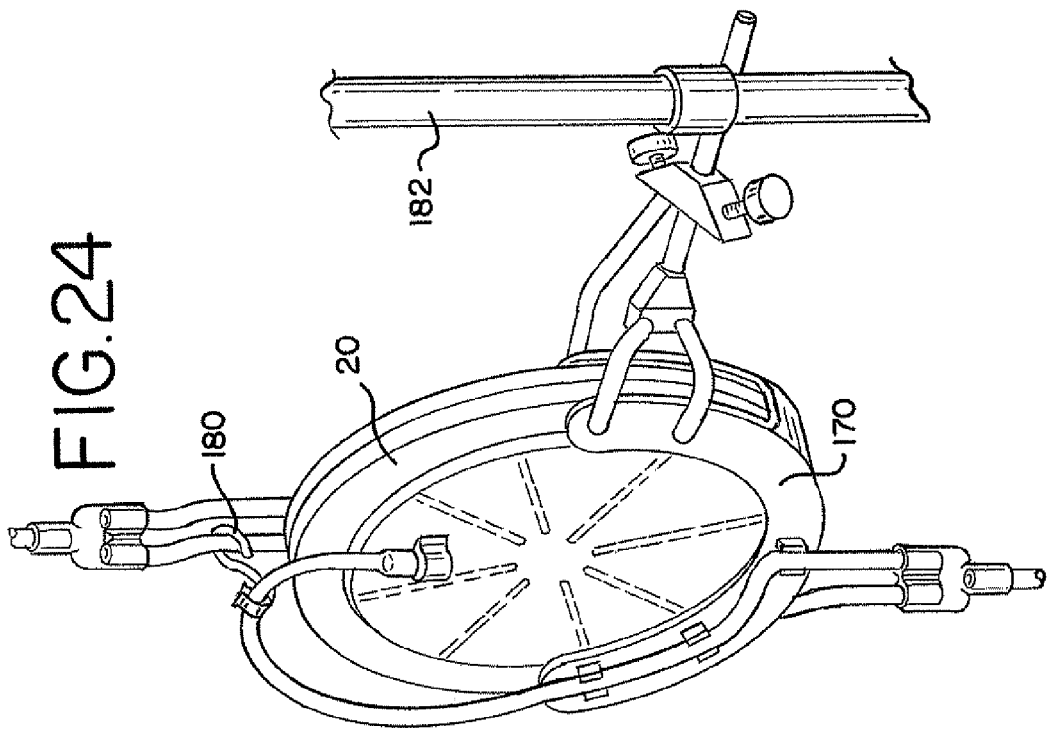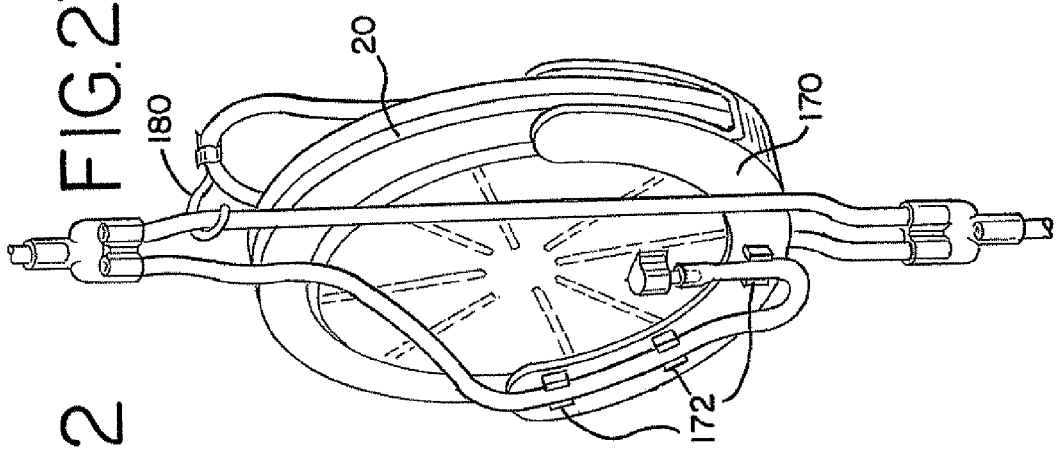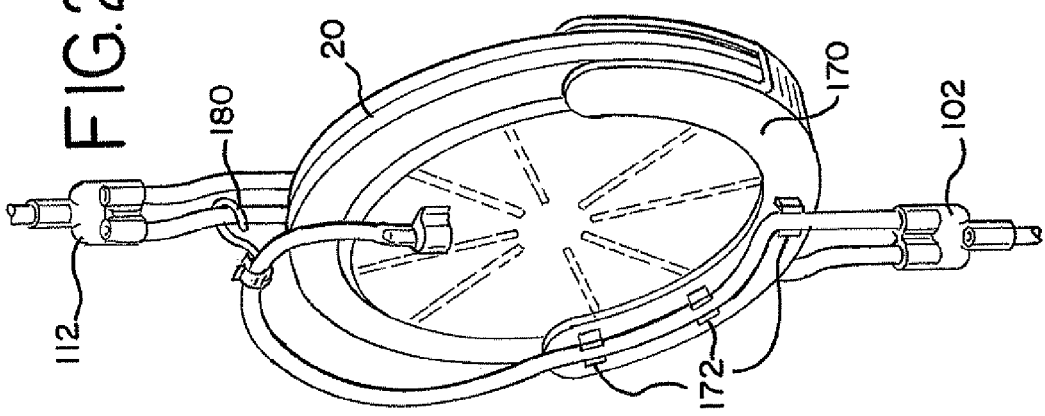

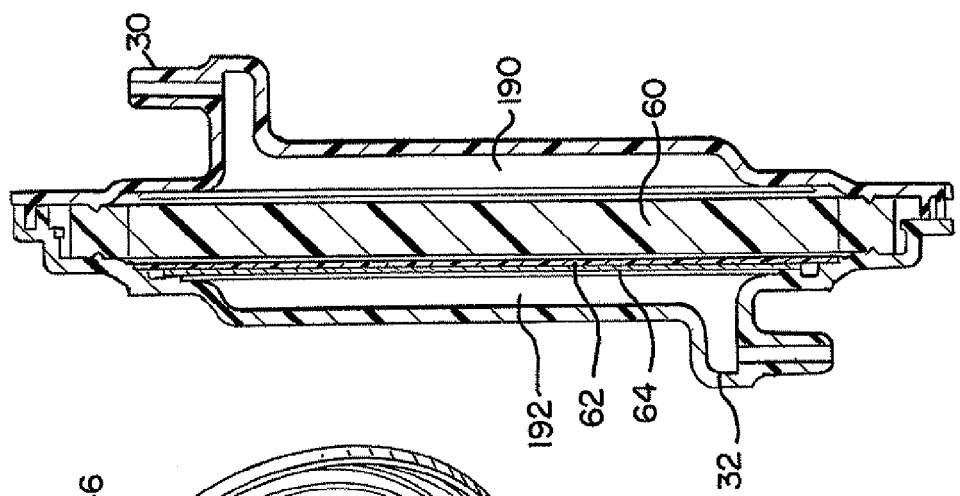
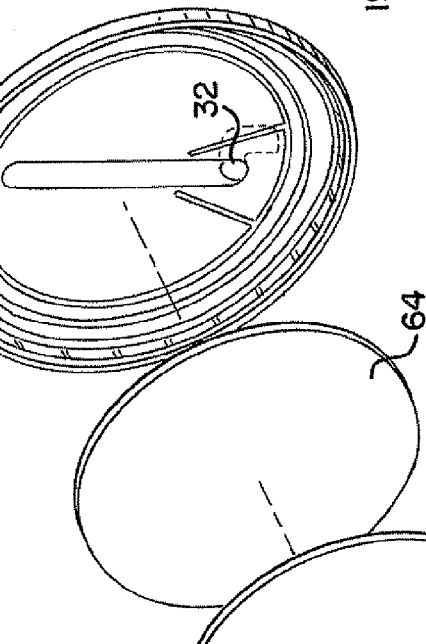
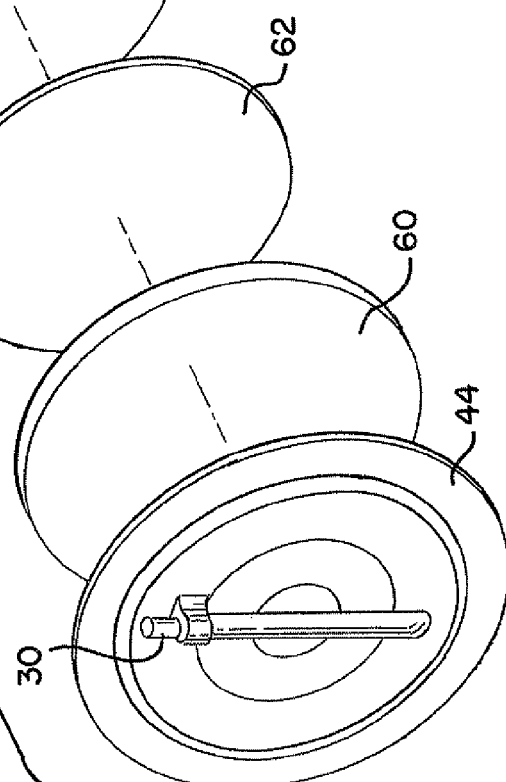
FIG. 25
FIG. 26

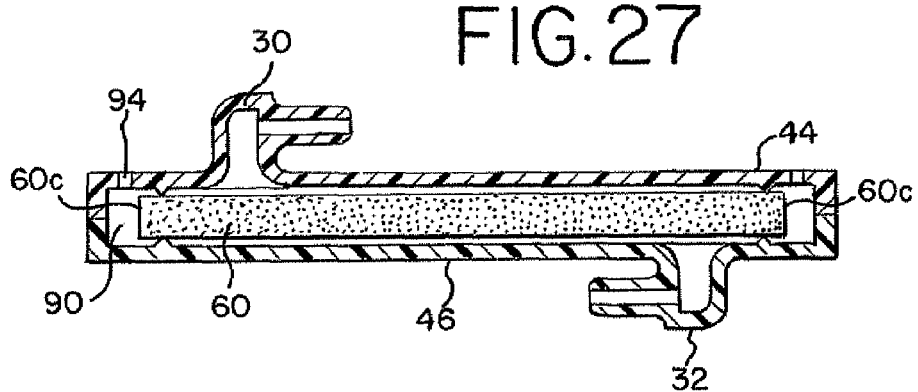
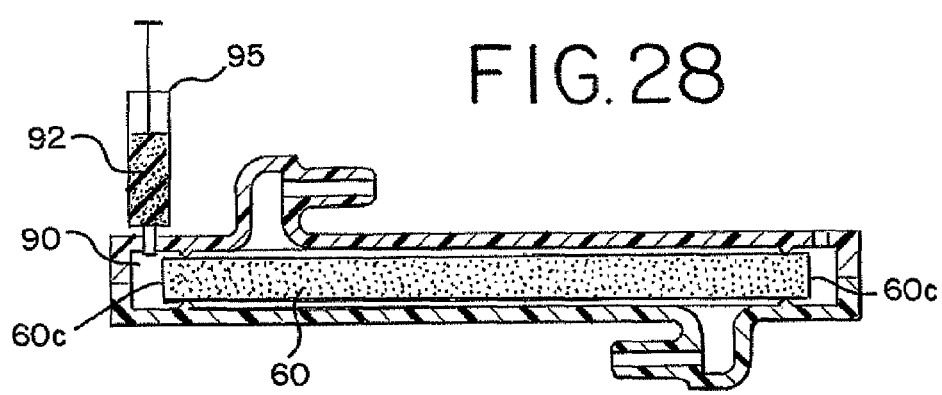
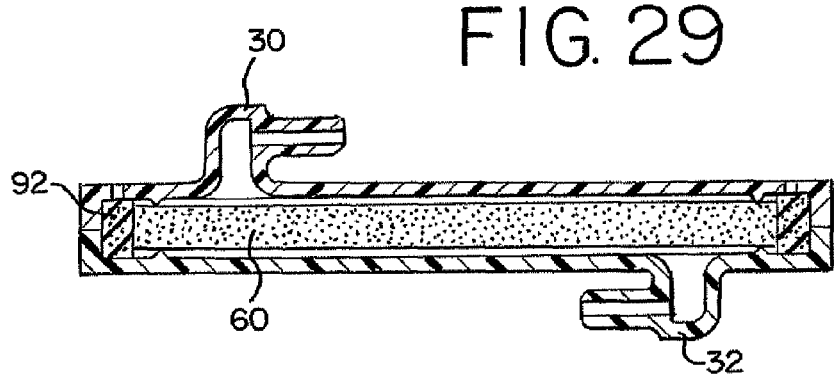

FLOW-THROUGH REMOVAL DEVICE AND SYSTEM USING SUCH DEVICE

The present invention is directed to a flow-through device for removing selected compounds and/or components from a fluid such as, but not limited to, a biological fluid. The present invention is also directed to fluid processing systems using such flow-through devices.

BACKGROUND OF THE INVENTION

Flow-through devices for removing compounds or other components from a biological fluid are known. For example, flow-through removal devices have been used in medical processing sets where the biological fluid is filtered to remove undesired blood components, such as leukocytes. Flow-through devices have also been proposed for use where the biological fluid has been treated with a solvent or chemical agent as, for example in a pathogen inactivation process.

In many pathogen inactivation processes, a chemical agent is typically added to the biological fluid to either (1) directly inactivate present pathogens or (2) inactivate present pathogens in combination with other means, such as light. Regardless of the method used, after treatment, it is desirable to remove unreacted chemical agents or by-products of the inactivation process from the biological fluid prior to its transfusion to the patient.

One example of such a pathogen inactivation processing system is described in U.S. patent application Ser. No. 09/325,599, which is incorporated herein by reference in its entirety. In the system described therein, fluid from a source container that has been treated in a pathogen inactivation process (e.g., photoactivation with ultraviolet light and a psoralen compound) is passed through a removal device and collected in a receiving container. The removal device includes a sorbent selected to remove residual chemical agent and/or by-products of the inactivation process.

Flow-through devices may also be used in the filtration of blood products to remove, for example, leukocytes from a collected blood product. An example of a fluid processing system that includes a leukoreduction filter in a flow-through arrangement is described in U.S. Pat. No. 6,358,420. Flow-through devices may also be used to remove treating agents used in the treatment of blood or a blood fraction, which agent is desirably removed from the fluid prior to further use of the fluid.

In the above-described examples, the removal device includes a housing and a removal media inside the housing. Regardless of the removal for which the device is used (i.e., leukoreduction, or removal of inactivation compounds or other agents), complete and uniform exposure of the fluid to the removal medium is important. To obtain the greatest efficiency for the removal medium, it is desirous for the fluid to come in contact with as much of the removal medium as possible. For example, to ensure substantially complete removal of the inactivating agent in the pathogen inactivation example described above, it is desirable that the fluid contact the removal media as completely as possible, without bypassing any part of the removal media. Likewise in a leukoreduction device, complete exposure is important to ensure substantially complete removal of leukocytes, which if otherwise transfused, may cause an adverse reaction in the recipient.

To further ensure substantially complete and uniform exposure of the fluid to the media, it is important that the removal media be maintained in a substantially fixed orientation. For example, in a processing set that includes a hanging-type filter where the flow is "top to bottom," very often, a natural twisting moment causes the filter to hang at an angle. As the weight below the filter changes (i.e., as the collection container fills), the moment increases and the angle changes. A device that tilts away from the central vertical axis may result in uneven distribution of the fluid across the removal media, resulting in incomplete exposure and removal of the undesired agents.

In addition to uniform and complete exposure of the fluid to the media, it is also important, to have substantial processing time consistency (i.e., reproducibility) from one device to the next.

It is also desirable that a device that meets the above performance requirements is also easy and economical to manufacture with a low rejection rate.

The above objectives are addressed by the present invention.

SUMMARY OF THE INVENTION

In one aspect, the present invention is directed to a flow-through device for removing selected compounds from a liquid. The device includes a housing having a first portion and a second portion that are joined together. Each of the first and second portions include outer walls and inner walls, with a compound removing medium disposed between the walls of the portions. One of the first or second portions includes an inlet port on the outer wall and the other of the first or second portions includes an outlet port on the outer wall. The inner wall of the first or second portions includes a peripherally extending tongue while the inner wall of the other of the first or second portions includes a peripherally extending groove for receiving the tongue.

In another aspect, the present invention is directed to a flow-through device for removing selected compounds from a liquid that includes a housing. The housing includes first and second outer walls defining an interior chamber between the walls. A compound removing medium is disposed within the interior chamber. In a preferred embodiment, the housing includes an inlet port on one of the outer walls and an outlet port on the other of the outer walls, wherein the location of the outlet port is diametrically opposed to the location of the inlet port.

In another aspect, the present invention is directed to a flow-through system for removing selected compounds or components from a fluid. The system includes a source container, including a fluid outlet and a receiving container including a fluid inlet. The system includes a compound removal device disposed between the source and receiving containers. The device includes a housing having first and second outer walls and a compound removing medium between the walls. The housing further includes a fluid inlet on one of the outer walls and located between the center of the device and the receiving container, and a fluid outlet on the other outer wall and located between the center of the device and the source container on the other outer wall. The system further includes a first tube providing a flow path between the source container and the device inlet and a second tube providing a flow path between the device outlet and the receiving container inlet.

In another aspect, the present invention is directed to a flow-through device for removing selected compounds from a liquid. The device is comprised of a housing having a pair of side walls and a peripheral wall defining a chamber. A removal medium is located within the chamber, the medium having an end wall terminating interior to the peripheral wall of the housing. A liquid impermeable barrier is located in the area of the chamber substantially between the medium peripheral end surface and the peripheral end wall of the housing.

In another aspect, the present invention is directed to a flow-through processing system for removing selected compounds or components from a fluid. The flow-through system includes a source container including a fluid outlet and a receiving container including a fluid inlet. A compound removal device is located between the source container and the receiving container. The housing includes a first and second outer walls and a compound removing medium between the walls. The housing includes a fluid inlet on the first outer wall, the inlet being located between the center of the first housing wall and the receiving container and a fluid outlet on the second outer wall located between the second housing wall center and the source container. The system also includes a tubing providing a flow path between the source container outlet and housing inlet and tubing providing a flow path between the receiving container inlet and housing outlet. The length of the flow path between the source container and the inlet is greater than the length of the flow path between the device outlet and the receiving container.

BRIEF DESCRIPTION OF THE DRAWINGS

FIG. 1 is a plan view of a fluid processing system including a flow-through removal device embodying the present invention.

FIG. 2 is a partial plan view of the fluid processing system of FIG. 1 showing the reverse side of the flow-through device.

FIG. 3 is a perspective view of the removal device embodying the present invention.

FIG. 4 is an exploded view of the flow-through removal device embodying the present invention.

FIG. 5 is a cross-sectional side view of the flow-through removal device of FIG. 1.

FIG. 6 is an enlarged, partial cross-sectional view of the flow-through removal device of FIG. 5.

FIG. 11 is a partial plan view of one embodiment of a fluid processing system including a flow-through removal device.

FIG. 12 is a partial side view of another embodiment of the fluid processing system.

FIG. 15 is a partial plan view of still another embodiment of a flow-through system including a flow-through removal device.

FIG. 16 is a plan view of the reverse side of the flow-through removal system and device of FIG. 15.

FIG. 19 is a perspective view of a removal device within the holder of FIG. 18.

FIG. 20 is a reverse perspective view of the holder and flow-through removal device of FIG. 19.

FIG. 21 is a cross-sectional view of the tubing channel of the holder of FIG. 19.

FIG. 22 is a perspective view of an alternative embodiment of the holder for supporting the flow-through removal device.

FIG. 23 is the perspective view showing the reverse side of the holder and flow-through removal device of FIG. 22.

FIG. 24 is an alternative arrangement of the holder and flow-through removal device of FIG. 22, including a connector attached to a vertical support pole.

FIG. 25 is an exploded perspective view of a further alternative embodiment of the flow-through removal device embodying the present invention.

FIG. 26 is a cross-sectional side view of the flow-through removal device of FIG. 25.

FIG. 27 is a cross-sectional side view of a removal device with removal medium disposed therein.

FIG. 28 is a cross-sectional side view of a compound removal device with a sealant being injected into the housing interior.

FIG. 29 is a cross-sectional side view of a removal device with a sealant filled gap.

DETAILED DESCRIPTION OF THE PREFERRED EMBODIMENTS

Figure 1A:
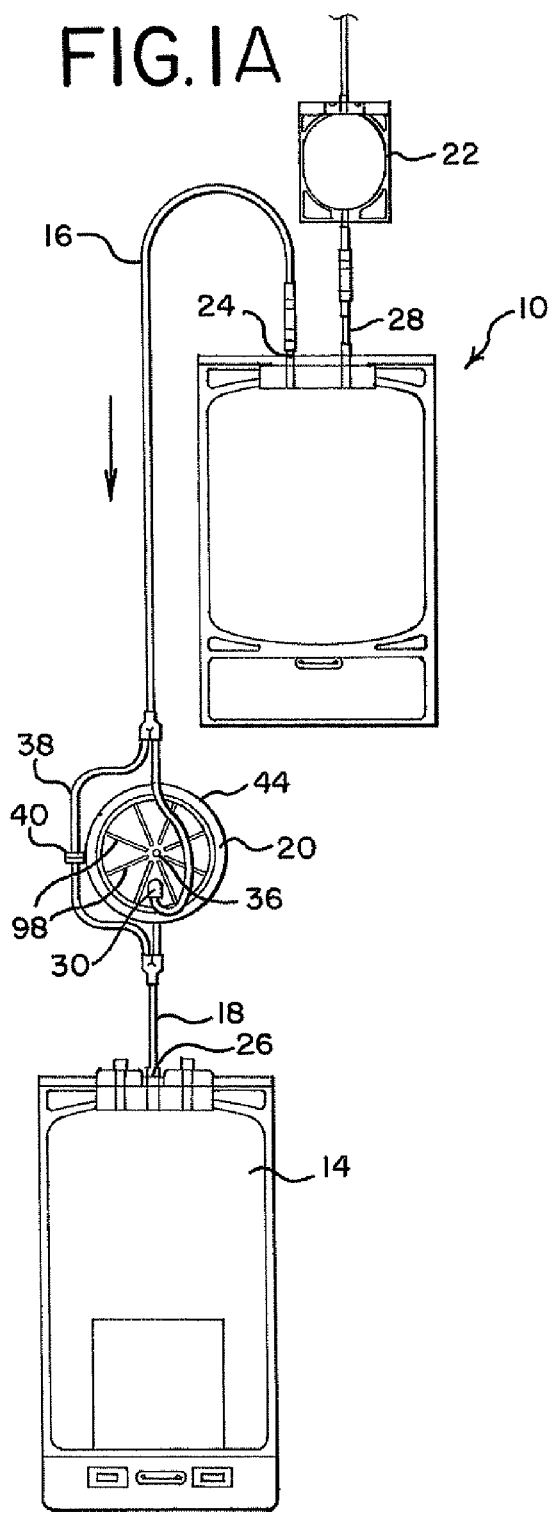
FIG. 1A is a plan view of an alternative fluid processing system with a flow-through removal device embodying the present invention.

Turning now to the drawings, FIG. 1 shows a flow-through fluid processing system embodying the present invention. The system may be used in any application where fluid is passed from a fluid source to a receiving container, and contact between the fluid and a treating, removing or filtering medium is desired.

In FIG. 1, there is shown a source container 12 for holding fluid. In one specific, yet non-limiting application, source container 12 may hold a biological fluid, such as blood or a component of blood. The system shown in FIG. 1 also includes a receiving container 14. A removal device 20 embodying the present invention is also shown and is typically located between and in flow communication with the source container 12 and receiving container 14.

Optionally, the system 10 may include additional containers. For example, in the embodiment shown in FIG. 1, system 10 includes an additional container 22 which may include an agent, useful in the treatment of the biological fluid. Specifically, in a non-limiting example, container 22 may include an agent useful in the pathogen inactivation of the biological fluid.

One example of a pathogen inactivation compound is a psoralen compound, such as, but not limited to, 5'-(4-amino-2-oxa) butyl-4,5',8-trimethyl psoralen as the pathogen inactivation compound. Examples of suitable psoralen compounds and methods of inactivating pathogens in biological fluid using psoralens are provided in U.S. Pat. Nos. 5,578,736 and 5,593,823, both of which are incorporated herein by reference.

Other examples of pathogen inactivating compounds include phthalocyanine derivatives, phenothiazine derivatives (including methylene blue or dimethyl-methylene blue); endogenous and exogenous photosensitizers such as alloxazines, isoalloxazines (including riboflavin), vitamin Ks, vitamin L, napththoquinones, naphthalenes, naphthols, pathogen inactivating compounds disclosed in U.S. Pat. Nos. 6,258,577, 6,268,120, and 6,277,337, which are incorporated herein by reference, or "Pen 110," which is made by V.I. Technologies, Inc. (which is also known as the Inactine™ compound).

Examples of pathogen inactivation compounds that may be useful in red blood cell pathogen inactivation methods include the pathogen inactivation agents disclosed above and those disclosed in U.S. Pat. No. 6,093,725 and U.S. application Ser. No. 09/539,226 filed Mar. 30, 2000, which is directed to the use of compounds having nucleic acid affinity and containing a mustard group, or mustard group equivalent or mustard group intermediate. U.S. Pat. No. 6,093,775 and U.S. application Ser. No. 09/539,226 are incorporated herein by reference. A preferred compound for red blood cell pathogen inactivation is p-alanine, N-(acridin-9-yl), 2-[bis(2-chloroethyl)amino] ethyl ester.

Returning to FIG. 1, container 22 is connected (and is in flow communication with) source container 12 via tube 28. Details of this illustrative system and of the pathogen inactivation process with which it is used are set forth in U.S. patent application Ser. No. 09/325,599, filed Jun. 3, 1999 and previously incorporated by reference.

As further shown in FIGS. 1 and 2, source container is connected to removal device 20 by a first tube 16. Tube 16 provides a flow path from source container 12 to removal device 20. One end of tube 16 is joined to outlet port 24 of container 12, and the other end to the inlet port 30 of device 20.

As shown in FIGS. 1 and 2, system 10 includes tube 18 which connects device 20 to receiving container 14. Specifically, one end of tube 18 is joined to inlet port 26 of container 14, and the other end is joined to outlet port 32 of device 20.

Figure 2A:
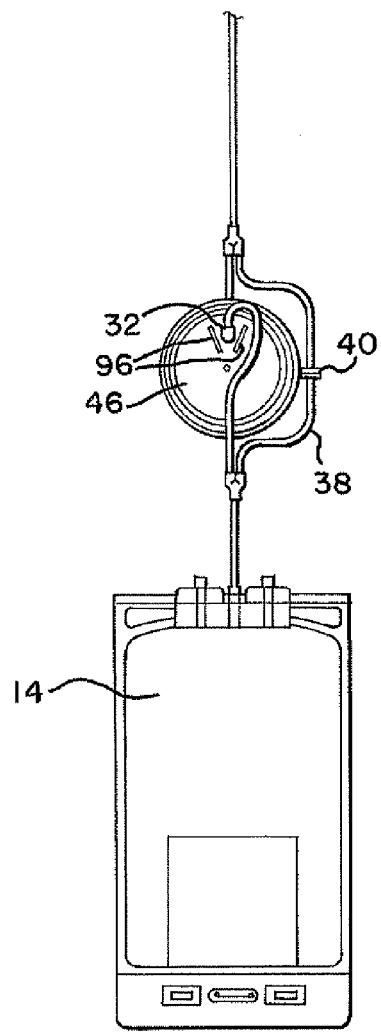
FIG. 2A is a partial plan view of the fluid processing system of FIG. 1A showing the reverse side of the flow-through device.

An alternative flow-through system 10 is shown in FIGS. 1A and 2A. The same reference numerals are used to identify the same features as those shown in FIGS. 1 and 2. In the embodiment shown in FIGS. 1A and 2A, it will be appreciated that the opening in inlet port 30 faces away from the center 36 (i.e., toward the periphery of the housing) of device 20. Similarly, the opening in outlet 32 faces away from the center 36 (and toward the housing periphery) of device 20. While the orientation of inlet port 30 and outlet port 32 as shown in FIGS. 1 and 2 is preferable, the embodiment shown in FIGS. 1A and 2A is equally suitable.

Regardless of the orientation of ports 30 and 32, a common aspect of both of the embodiments shown in FIGS. 1 and 1A is the location of inlet and outlet ports of device 20 relative to the device center 36 and containers 12 and 14. In each of the embodiments, inlet port 30 is located between the center 36 of device 20 and receiving container 14. The outlet 32 is located between the center 36 and source container 12. This results in a flow through device 20 that is directionally reversed relative to the flow through the remainder of the system 10. Thus, fluid enters inlet port 30 and is forced to flow "up" to outlet 32. It has been discovered that this reversed flow, at least in part, reduces the time required for a fluid to pass through device 20, provides more reproducible flow from device to device, and provides more complete exposure of the fluid to the removal media inside device 20.

Figure 30:
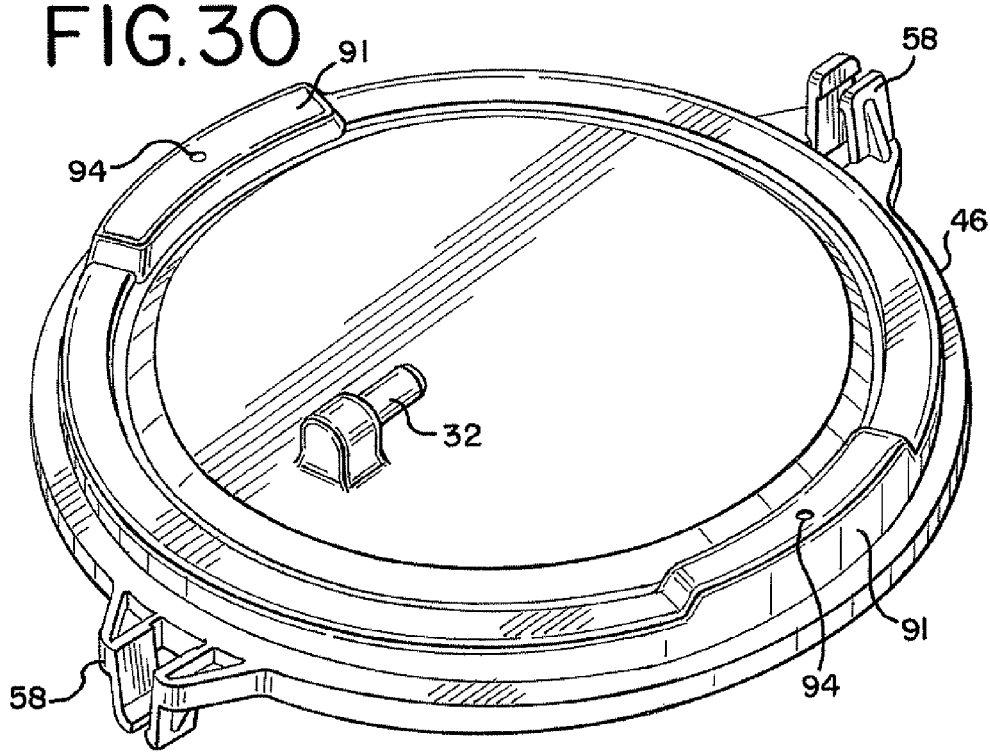
FIG. 30 is a perspective view of one portion of the removal device housing with sealant reservoirs and injection apertures.

Turning now to FIGS. 3, 4, and 5, there is shown a removal device 20 embodying the present invention. In a preferred embodiment, device 20 is comprised of a housing 42 made of two separate portions 44 and 46 that are joined together. Each portion 44 and 46 includes an outer surface, identified by 50 and 52 (see FIG. 5) and/or inner surfaces, identified by 54 and 56, respectively. As shown in FIG. 4-6 and FIGS. 35-36, portion 46 provides a base for receiving removal media 60 and optional filters 62 and 64 (described below). Thus, housing portion 46 has some depth to it, with multiple concentric flats 82, 84 and 89 (also described below) at different depth levels on which removal media 60 and optional filters nest. As shown in FIG. 6, portion 46 is comprised of a generally planar side wall and peripheral end wall 57. Housing portion 42 may be more in the form and shape of a flat cover member with no significant depth. As shown in FIG. 4, portion 44 includes inlet port 30 and portion 46 includes outlet port 32. As shown in FIG. 30, portions 44 and 46 may optionally include alignment tabs 48 to ensure proper mating of portions 44 and 46 during assembly.

Housing 42 is preferably made of a hard plastic that can be injection molded. The material used for housing 42 should be suitable for sterilization by known forms of sterilization such as gamma or electron beam radiation. The material should also be amenable to preferred sealing operations such as, but not limited to, ultrasonic welding. Examples of suitable materials include polymethylmethacrylate (PMMA) and acrylonitrile butadiene styrene (ABS). As shown in FIGS. 3-5, one of the housing portions 44 or 46 may include a retaining member 58 for receiving tubing 16 and/or 18 (discussed in more detail below).

As shown in FIG. 4, device 20 preferably includes one or more treating or removal media (e.g., disk 60) placed between inner surface 54 and 56 of device 20. As fluid enters device 20 through inlet port 30, it comes into contact with media 60. The fluid permeates the media and travels across the surface 60a thereof before exiting through outlet 32. In one non-limiting example, removal media 60 may be selected for removing unwanted components from a fluid. In a pathogen inactivation fluid processing system of the type described in U.S. patent application Ser. No. 09/325,599, the medium may be a sorbent media for removing unreacted pathogen inactivation compound, by-products of the pathogen inactivation treatment and other compounds and substances, including other pathogenic compounds.

As described in U.S. patent application Ser. No. 09/325,599, the removal media may be in the form of a disk made of, preferably, divinylbenzene styrene particulate that is finely ground and combined with a binding material, such as polyethylene or a blend thereof. This combination is sintered, resulting in disk 60 shown in FIGS. 4-6 having side surfaces 60a and 60b and peripheral end surface 60c. Disks of this type are available from Porex Technologies of Fairburn, Ga. with particulate provided by the Purolite Company of London, United Kingdom.

Of course, the removal media 60 described is not limited to the materials identified above. The medium can be made of any material, sorbent or otherwise, that can remove selected compounds or agents from the fluid. Examples of materials useful in the removal of compounds and agents are provided in U.S. Pat. No. 6,544,727 and U.S. Patent Application Publication Nos. US 2001/0018179 A1 and US 2001/0009756 A1, all of which are herein incorporated by reference. The medium can also be a filtration medium used to capture (other than by sorption) unwanted compounds or components. For example, the medium 60 may be used to capture leukocytes and remove them from the biological fluid.

As shown in FIG. 4, device 20 may include additional inserts for filtration and removal of compounds or components. For example, in an embodiment where device 20 is used in a pathogen inactivation treatment to remove residual agents and by-products of the inactivation process, it may be preferable to include one or more additional filtration media 62 and 64. Filters 62 and/or 64 may be included to capture any loose particulate from removal media 60. Filters 62 and 64 may be of conventional type as, for example, nylon mesh or, more preferably, polyester mesh with a pore size of between 0.2 and 0.8 microns. Although two filter elements 62 and 64 are shown, one filter element may be sufficient.

Figure 32:
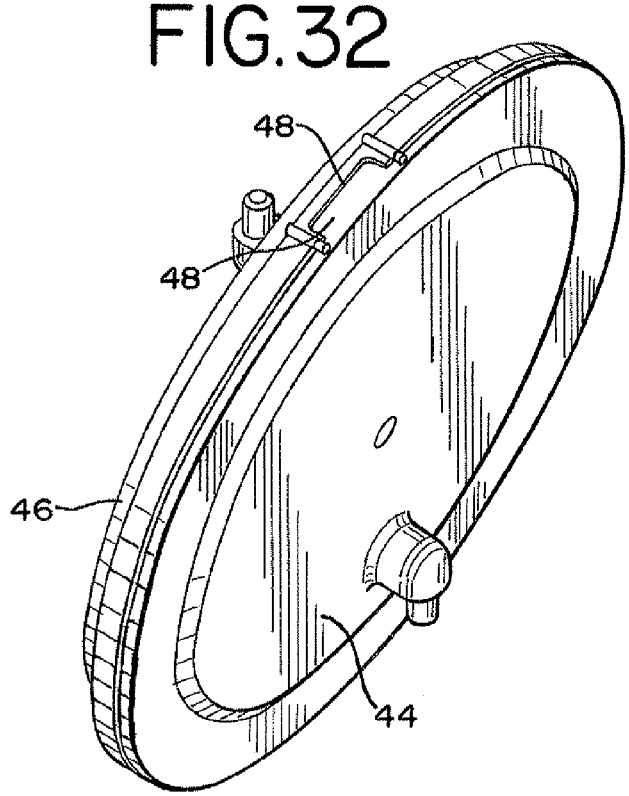
FIG. 32 is a perspective view of one embodiment of an assembled removal device.

As shown and previously described, housing 42 of device 20 is preferably made of two portions 44 and 46 joined together with removal medium 60 (and one or more filter media 62 and 64) enclosed within housing 42. In a preferred embodiment, portions 44 and 46 are joined to each other at or near their outer peripheries. Proper alignment of housing portions 44 and 46 may be ensured by aligning alignment tab 57 with retaining member 58. (Alternative and optional alignment tabs 48 are also shown in FIG. 32). Portions 44 and 46 may be joined together by sealing together inner surfaces 54 and 56 (of portions 44 and 46).

Preferably, portions 44 and 46 may be attached together by a mating tongue and groove arrangement. FIGS. 6 and 30-33 show the preferred mating arrangement. Inner surface 56 of portion 46 provides a groove 68 near the periphery of inner surface 56. Groove 68 is continuous along the entire periphery of housing portion 46. With reference to FIG. 6, groove 68 is sized to receive outwardly extending tongue 70 on inner surface 54 of housing portion 44. Like groove 68, tongue 70 is continuous along the entire outer periphery of portion 44.

During assembly of device 20, tongue 70 is inserted into groove 68. The area of the tongue and groove fitment is then preferably exposed to a sealing means. In a preferred embodiment, the sealing procedure may include an ultrasonic device for sonic welding and fusing of tongue 70 and groove 68. Other forms of welding or sealing, known to those of skill may also be used. The energy from the sonic weld melts the plastic parts of groove and tongue 68 and 70 and fuses them together, as shown in FIG. 32, thereby forming a permanent seal of portions 44 and 46.

Figure 33:
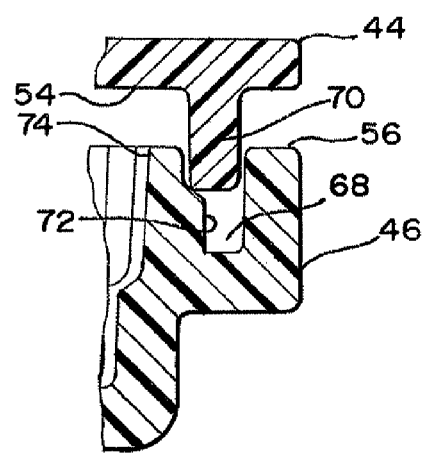
FIG. 33 is a partial, cross-sectional view of the tongue and groove engagement prior to welding.
Figure 34:
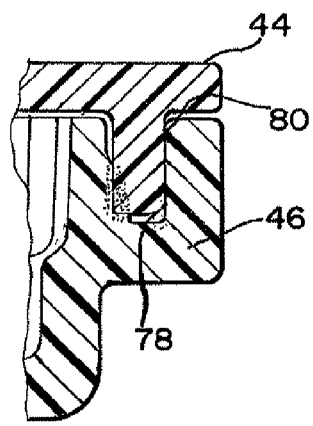
FIG. 34 is a partial, cross-sectional view of the tongue and groove welded together.

As shown in FIGS. 6 and 33, inner groove wall 72 includes an outwardly extending shoulder 74. During assembly of device 20, tongue 70 first comes into contact with shoulder 74 of groove 68. During welding these areas of tongue and groove 68 are first to physically fuse together to provide the seal. As further shown in FIGS. 6 and 34, the tongue 70, once inserted into groove 68 leaves outer and lower gaps 78 and 80. These gaps are provided to receive melt from the sonic welding process and reduce stress on the housing 42 which otherwise could lead to cracks in the housing.

Figure 35:
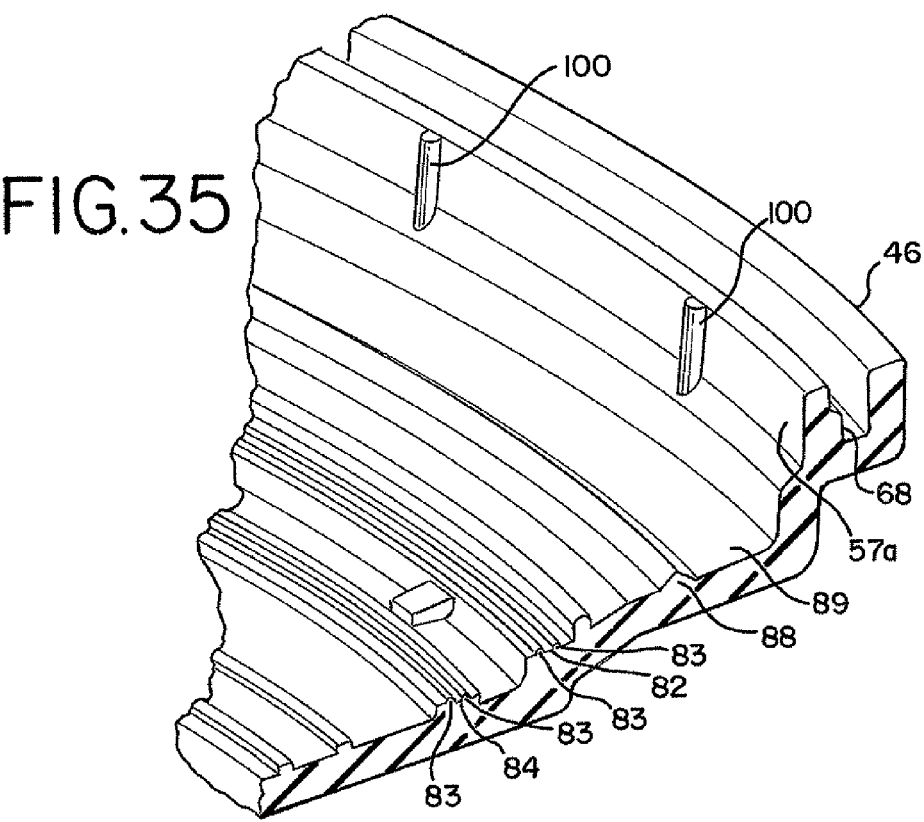
FIG. 35 is a perspective view, shown in cross-section, of a part of the outlet housing portion.
Figure 36:
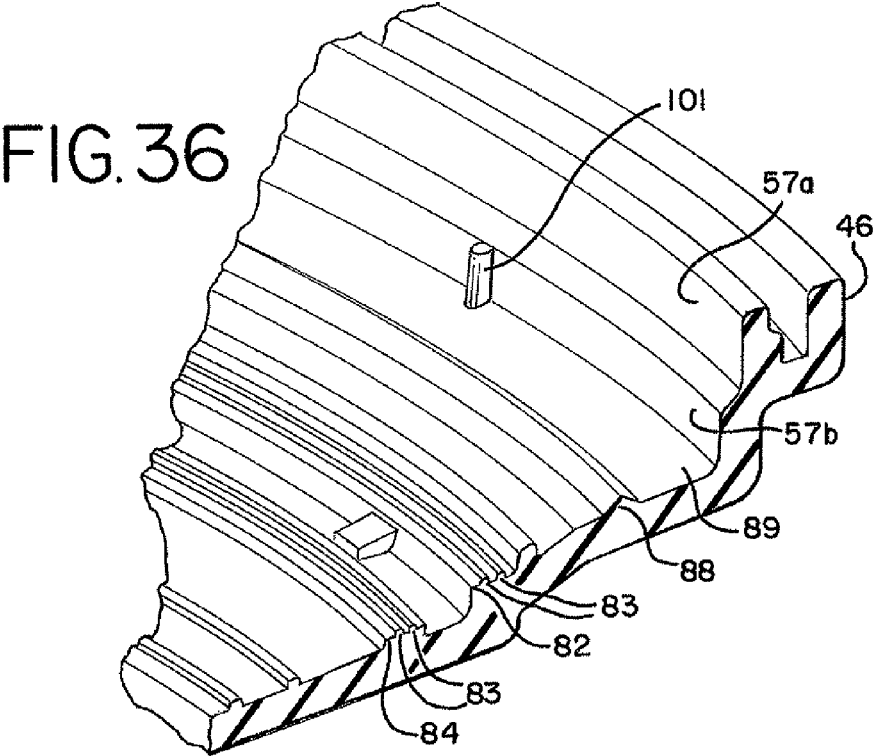
FIG. 36 is a perspective view, shown in cross-section, of a part of the outlet housing portion with an alternative rib arrangement.

As best seen in FIGS. 35-36, inner surface 56 of portion 46 may further include nesting shoulders or flats 82 and 84 on which filter media 62 and 64 are placed. Peripheral portions of filters 62 and 64 rest on flats 82 and 84 which may be continuous along the entire periphery of housing portion 46. Filters 62 and 64 may be adhered to inner surface 46 by known adhesion techniques. However, preferably, filters 62 and 64 are sonic welded to flats 82 and 84 along the peripheries thereof. Flats 82 and 84 may further include energy directors 83. Energy directors 83 may be raised, triangular surfaces, as shown in FIG. 33, and as will be recognized by those of skill in the art. Energy directors 83 assist in providing a firm weld between filter 62 and/or 64 and housing 46.

As further seen in FIG. 6 (and 35 and 36), one or both housing portions 44 and 46 may include a continuous gripping member(s), or seal ring(s) 86 (and 88). As shown in the Figures, rings 86 and 88 may be raised surfaces that extend from inner surfaces 54 and 56 near the peripheries of portions 44 and 46. In a preferred embodiment, seal rings 86 and 88 are located between center 36 of device 20 and the tongue and groove assembly 70 and 68 described above. As shown in FIG. 6, seal rings 86 and 88 partially compress removal medium 60 and substantially prevent liquid from traversing and bypassing medium 60. Preferably, rings 86 and 88 may terminate in a pointed end to better grip removal medium 60.

Figure 31:
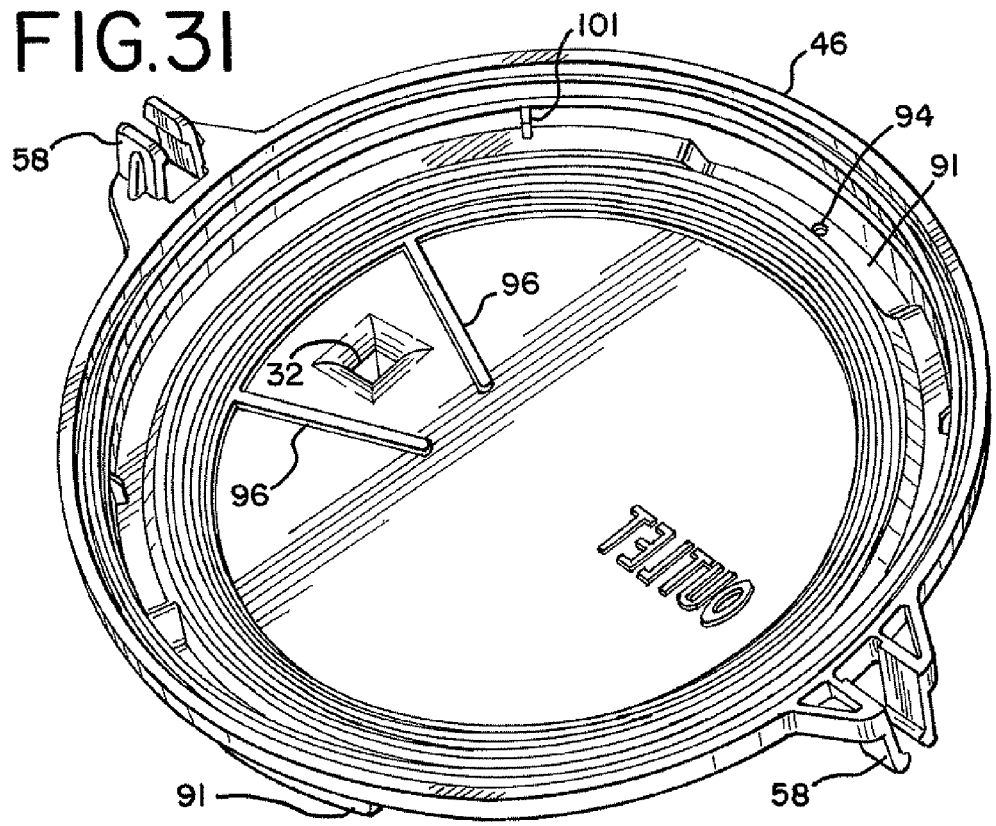
FIG. 31 is a perspective view of the reverse side of housing portion of FIG. 30.

For additional assurance that liquid is not bypassing medium 60, the gap 90 remaining between medium 60 and housing 42 may be substantially filled with a liquid impermeable barrier. Shown in FIGS. 27 and 28 is one method of sealing or substantially filling gap 90 and preventing any unintentional liquid bypass. Turning briefly back to FIG. 6, gap 90 surrounds removal media (disk) 60 in the area between rings 86 and 88 and the inner surfaces 54 and 56 of the side walls and peripheral end wall 57 of housing 42. As shown in FIGS. 27 and 28, a sealant 92 may be injected into gap 90. Injection ports 94 may be provided in housing portions 44 and/or 46. Sealant 92 may be injected by syringe 95 or any other means. As shown in FIGS. 30 and 31, housing portion 46 may also include one or more reservoir(s) 91 for receiving a quantity of sealant. Reservoir(s) 91 provide(s) a space for a sufficient quantity of sealant to effectively seal gap 90.

Suitable sealants may include epoxies, RTVs, hot melts, polyurethane, EVA-based hot melts, silicones or other plastics, such as acrylic polymers. A preferred sealant is an EVA/wax hot melt available from Bostik Findley of Wauwatosa, Wis. under the name Bostik H1714. The sealant may also be a gel that remains semi-solid after being injected. In any event, introducing sealant into gap 90, as shown in FIG. 29, effectively prevents liquid from bypassing removal medium 60.

Figure 37:
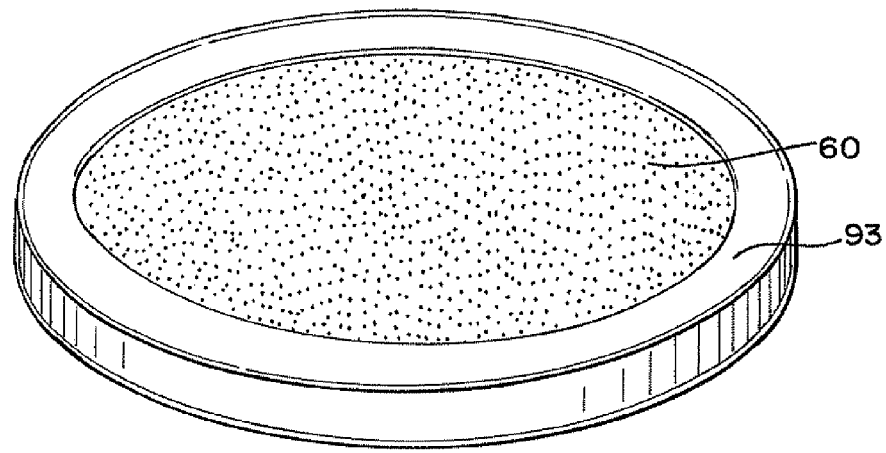
FIG. 37 is a perspective view of an alternative embodiment of the removal media with a ring of binder material around the perimeter of the media disk.
Figure 38:
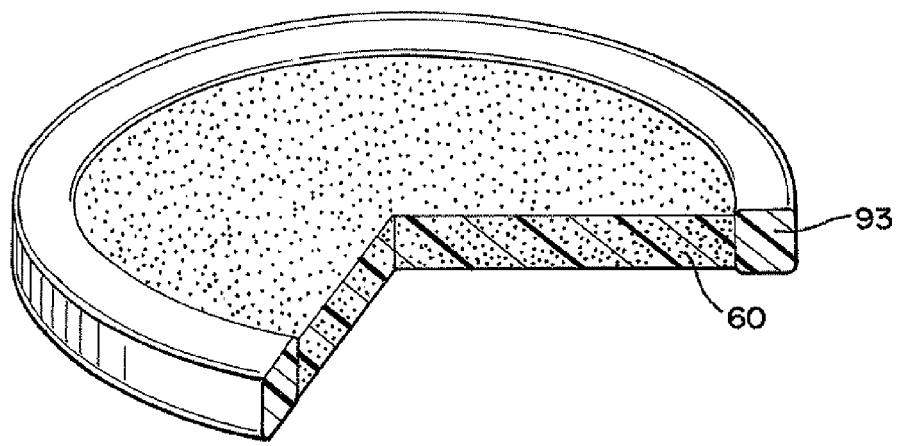
FIG. 38 is a perspective view of the disk of FIG. 37 with a portion cut away to show a cross-sectional view of the disk and ring.

Preventing liquid bypass of removal media 60 can also be accomplished by providing the disk of removal media 60 with a preformed sealing ring 93 or gasket around the perimeter of medium 60, as shown in FIGS. 37 and 38. In one such alternative embodiment, ring 93 may be made of a suitable binding material that can be applied to the outer perimeter of removal medium disk 60. Ring 93 can be molded onto disk 60 during or after manufacture of the disk. For example, in one embodiment, ring 93 may be molded during the sintering of removal medium disk 60.

Figure 39:
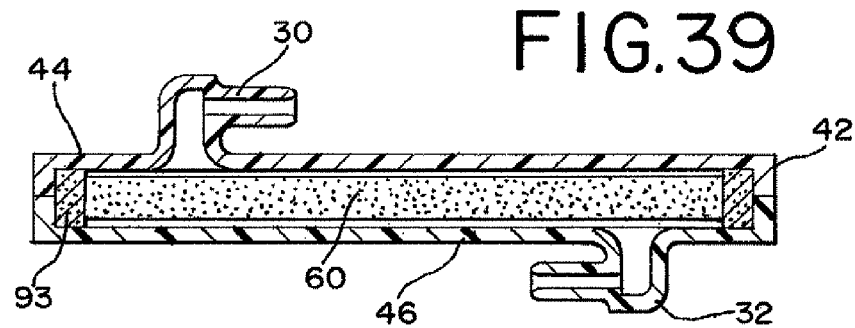
FIG. 39 is a cross-sectional side view of a removal device including the removal disk of FIG. 37.

Ring 93 should have a thickness substantially equal to the gap 90 formed by housing portions 44 and 46 when the portions are brought together to form housing 42, as shown in FIG. 39. Any binder that is substantially liquid impermeable and biocompatible and can be molded onto or with the disk is suitable. In one example, the ring 93 may be made of a binding material made of a polymeric material, such as, but not limited to, polyethylene. A preferred polyethylene is ultra high molecular weight polyethylene (UHMWPE). The UHMWPE may be blended with other compounds, however, a 100% UHMWPE is preferred.

In a variant of the above-described embodiment, ring 93, or a suitable sealant or binding material may be formed first and placed in a sintering mold cavity. The removal media can then be sinter-formed inside the molded disk, resulting in a structure substantially similar to that shown in FIGS. 37 and 38. The outer ring 93 can be molded sonically, or otherwise, to housing 42. Where housing 42 is made of an acrylic-based material, a suitable material for ring 93 is acrylic, which can then be welded to housing 42.

Figure 40:
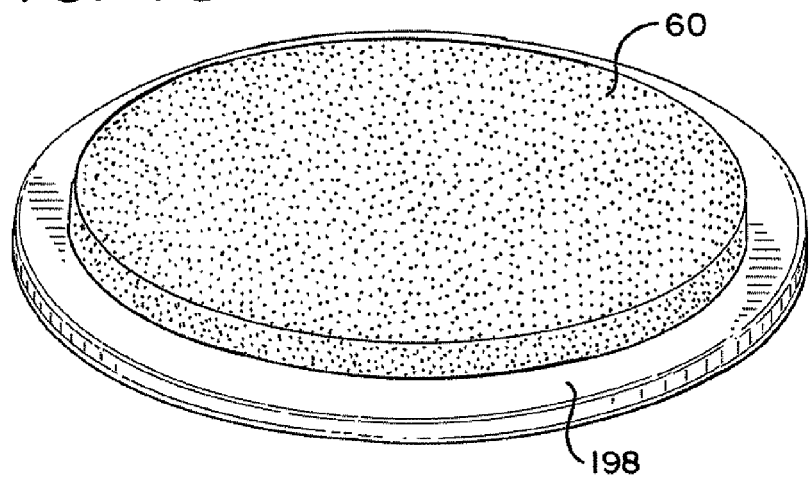
FIG. 40 is a perspective view of an alternative embodiment of the removal media with an annular gasket around the perimeter of the media disk.
Figure 41:
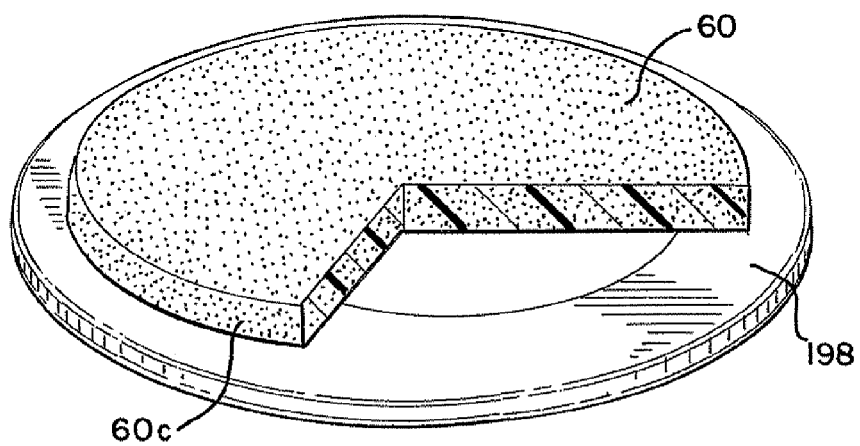
FIG. 41 is a perspective view of the disk of FIG. 40 with a portion of the removal media cut away to show the gasket.
Figure 42:
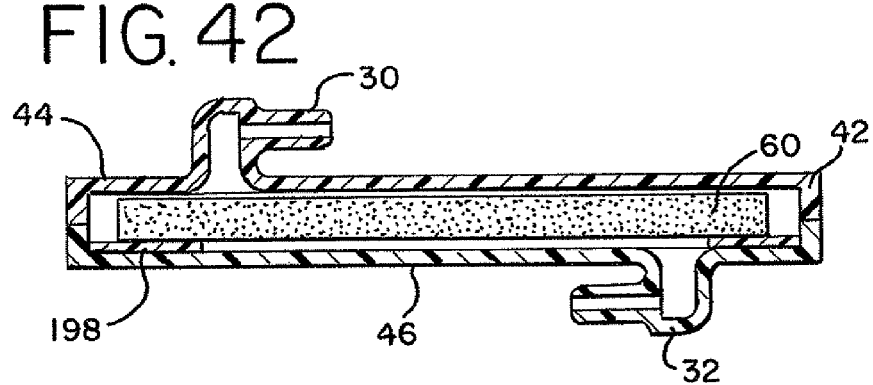
FIG. 42 is a cross-sectional side view of a removal device including the removal media of FIG. 40.

In another alternative shown in FIGS. 40-42, a thin gasket 198 made of a liquid impermeable and biocompatible material can be placed inside a mold cavity. The removal medium disk 60 can be sinter formed on top of the gasket. The gasket may be sealed to housing 42 by solvent bonding, ultrasonic welding or other known sealing techniques. Gasket 198 may be attached to the surface of disk 60 adjacent to the outlet port 32 of housing 42, as shown in FIG. 42. Preferably gasket 198 extends substantially to the outer end wall of the annular gap 90 in housing 42, thereby preventing any liquid that may not have contacted removal disk 60, from exiting through the outlet port 32. A suitable gasket material can be any polymeric material or blend of polymeric material that is also biocompatible. An example of one such material is an ethylene vinyl acetate composition.

Still other alternatives include depositing or printing a hotmelt adhesive onto the perimeter of the medium disk 60, shrink-fitting a film around the perimeter of medium disk 60 or dipping the perimeter of the medium disk in a PVC plastisol.

Figure 43:
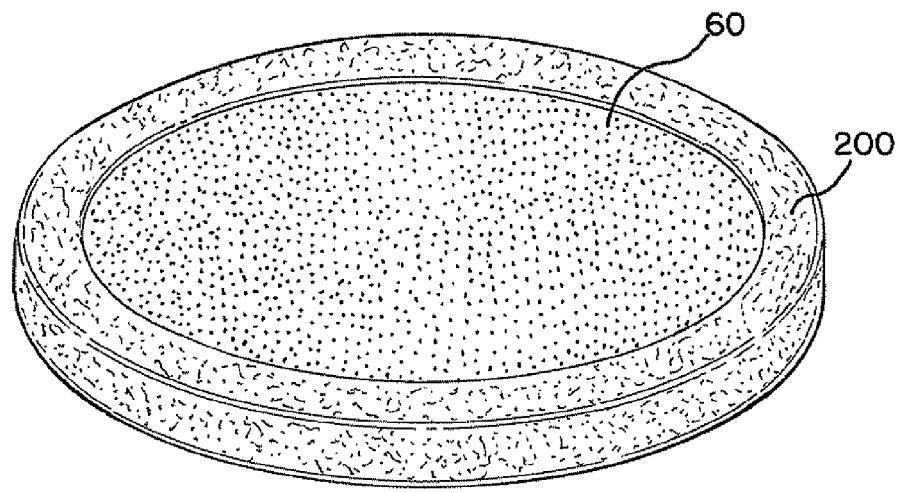
FIG. 43 is a perspective view of the removal media disk with an impermeable skin around the outer perimeter of the media disk.
Figure 44:
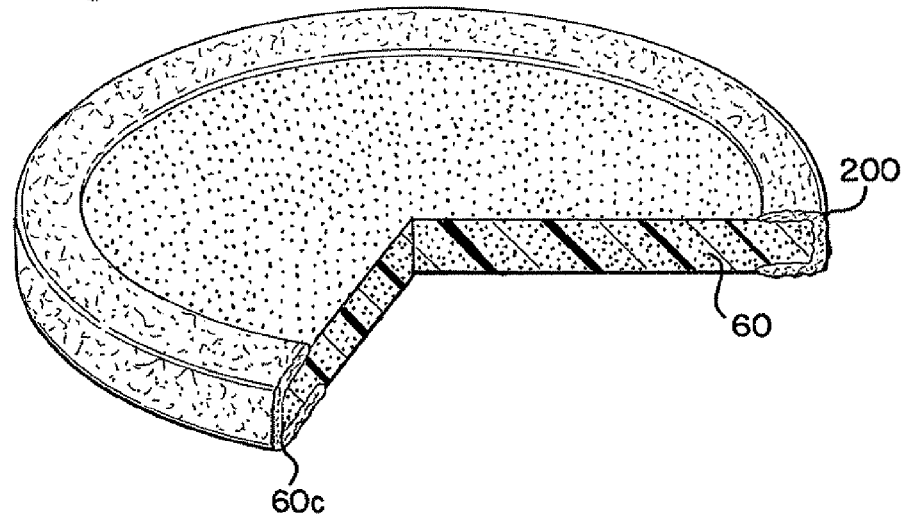
FIG. 44 is a perspective view of the removal media disk of FIG. 43 with a portion cut-away to show a cross-sectional view of the media disk.
Figure 45:
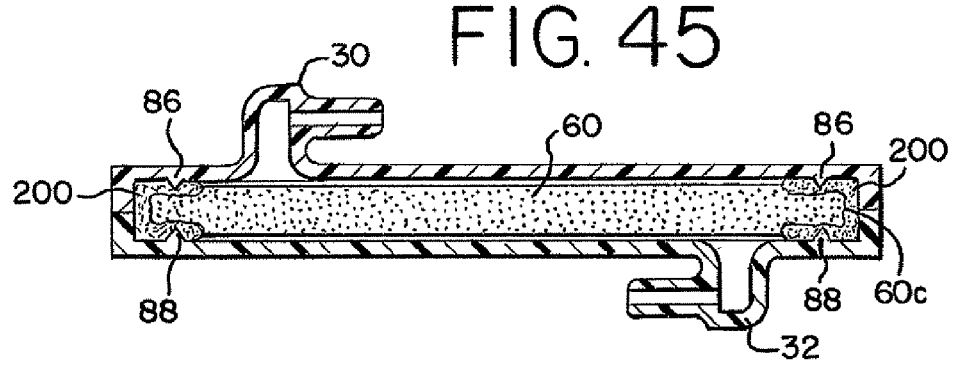
FIG. 45 is a cross-sectional side view of a removal device including the removal media of FIG. 43.

In yet another alternative that does not require applying a sealant around to the disk 60 perimeter, the end surface 60c of the removal medium disk 60 may be treated to provide a liquid impermeable peripheral edge. In one embodiment, disk 60 perimeter may be exposed to a high temperature, such as, approximately 120° C. to create an impermeable skin around the perimeter. A skin can be formed by rotating the disk and exposing the peripheral edge of disk 60 to a hot air source or placing the disk in a hot-mold press to further form it after sintering. As shown in FIG. 43, skin 200 is formed around the outer perimeter and peripheral edge of medium disk 60 with some of skin 200 overlapping the sorbent material on the outer surface of disk 60. Preferably, skin 200 extends over outer surface of disk 60 such that seal rings 86 and 88, previously described, contact the skin-covered portion of disk 60, as shown in FIG. 45.

Turning briefly back to FIG. 1A, one or preferably both of housing portions 44 and 46 may include a plurality of ribs 96, 98. Ribs 96, 98 may be raised surfaces that extend from inner surfaces 54 and 56, respectively. In a preferred arrangement, portion 46, which includes outlet port 32, includes two or more ribs 96 placed at or near port 32 as shown in FIG. 31. Ribs 96 prevent filter 64 from blocking outlet port 32.

Housing portion 44 may also include a plurality of ribs 98. Ribs 98 may be raised surfaces that extend from inner surface 54 and provide strength and additional support for housing 44 during assembly. This may be particularly desirable when device 20 is joined by ultrasonic welding. Additionally, ribs 96 may prevent removal device 60 from adhering to the inner wall 54 of portion 44 (and possibly blocking inlet port 30). The plurality of ribs 98 may be spaced and arranged in any desirable configuration. For example, ribs 98 may be spaced from each other in parallel across the surface of inner wall 54. Other arrangements are also possible. In a preferred embodiment, ribs 98 are radially spaced extending from a point near the center 36 of device 20 (like spokes on a wheel), as shown in FIG. 1A.

As shown in FIG. 35, a plurality of ribs may also be provided in housing portion 46. As shown in the Figures, ribs 100 line the outer perimeter of portion 46 at the inner surface 56 adjacent to groove 68. More specifically ribs 100 support the peripheral upstanding wall segment 57a that defines, in part, groove 68. Ribs 100 provide strength to the housing and prevent groove 68 from deflecting during, for example, ultrasonic welding. Alternatively, as shown in FIG. 36, a series of ribs 101 may also be provided along the peripheral wall 57, and more specifically wall segment 57b. Ribs 101, which may be more widely spaced (and, therefore, fewer in number) than ribs 100 provide a reference point for locating disk 60 on flat 89. It will be understood that housing portion 46 may include either one set of ribs 100 or 101, or may include both sets.

Figure 7:
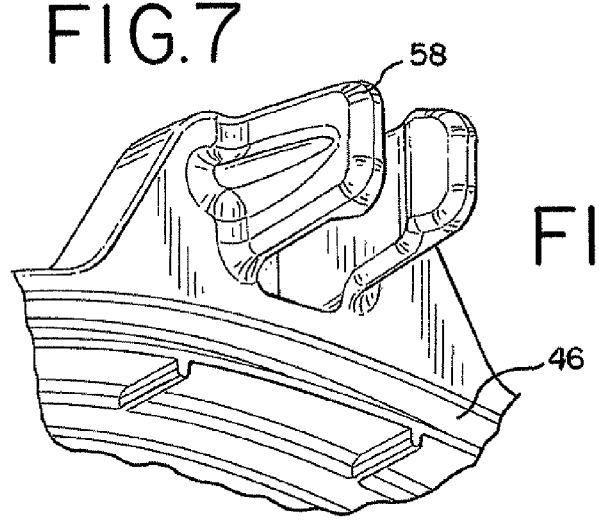
FIG. 7 is a partial perspective view of the retaining clip on the housing of the flow-through removal device embodying the present invention.
Figure 8:
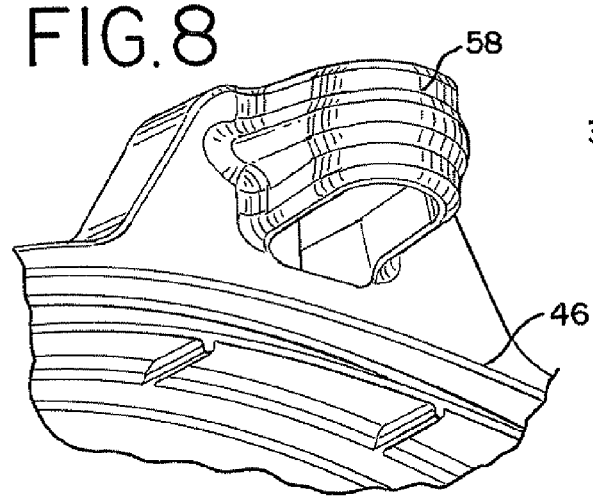
FIG. 8 is a partial perspective view of a retaining loop on the housing of the flow-through removal device embodying the present invention.
Figure 9:
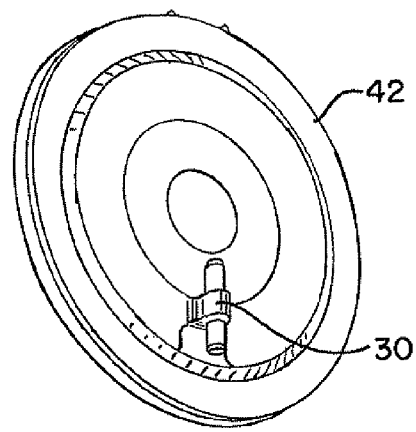
FIG. 9 is a perspective view of one portion of the flow-through removal device embodying the present invention including a version of the inlet port.
Figure 10:
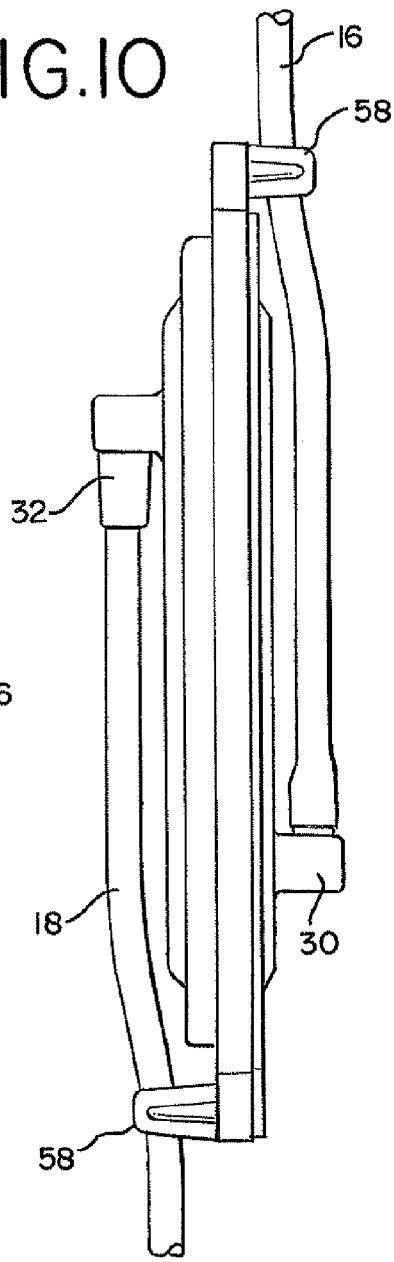
FIG. 10 is a side view of one embodiment of a flow-through removal device.

With reference to FIGS. 3 and 7, device 20 may include one or more retaining members 58 on housing 42. As shown in the Figures, retaining members 58 may be integral with the housing portion 46. Retaining member 58 may be in the form of a two-pronged clip, as shown, for example, in FIG. 7. During assembly of the processing system 10, tubing 16 or 18 is press fit into the gap between the prongs of the clip, as shown in FIG. 10. Retaining member 58 is substantially aligned with port 30 and/or 32. Alternatively, retaining member 58 may be a closed loop through which the tube 16 or 18 is threaded. Retaining members hold tubing 16 and 18 adjacent to housing 42 and assist in maintaining housing 42 in a substantially vertical orientation. As mentioned above, maintaining the vertical orientation of housing 42 is important to ensuring uniform exposure of the fluid to the removal media of device 20.

FIGS. 11-16 and 26 show different fluid circuits and tubing configurations for directing flow through the flow-through fluid processing set 10 of the present invention. Typically the processing set is suspended from, for example, an IV pole to allow for gravity induced flow of fluid through the system. In FIG. 11, there is shown a portion of the flow-through fluid processing system 10. As shown therein, the flow-through fluid processing system 10 includes a housing 42. It will be understood that the compound removal device 20 of the embodiments shown in FIGS. 11-16 is located between source container 12 and receiving container 14 (as shown in FIGS. 1 and 1A). Thus, container 12 will be "above" the compound removal device 20 and receiving container 14 will be "below" the compound removal device.

As shown in FIG. 11, device 20 includes an inlet port 30 on one side of housing 42 and outlet port 32 on the opposite side of housing 42 (e.g., outer surfaces 50 and 52). As shown in the Figures, in the preferred arrangement, ports 30 and 32 are diametrically opposed such that inlet port 30 is in the lower end of one portion, whereas outlet port 32 is located in the upper end of the other portion. As discussed above, placement of inlet port 30 in a location where fluid must then flow "up" to the outlet is preferred and provides improved and consistent processing times, and ensures more complex exposure of the fluid to the media when compared to other inlet/outlet arrangements.

In one embodiment, such as the one shown in FIG. 1, where the opening of inlet port 30 faces the center 36 of device 20, tube 16 communicates directly with inlet port 30 in a straight path. As shown in FIG. 1A, where the opening to inlet port 30 faces away from source container 12 (and from the center 36 of the device 20) flow path must be re-oriented to allow entry of fluid into device 20. Thus, as shown in FIG. 11, where tube 16 is not attached to inlet port 30 through a straight path (as in FIG. 1), the direction of flow must be reversed.

For example, a flow through fluid processing system 10 where flow enters device 20 through an outlet that faces away from source container 12, may include a flow conduit to allow fluid entry. In this embodiment, the conduit diverts the flow in a direction that is approximately 180°0 turned from the direction of flow from container 12.

Thus, in the embodiment shown in FIG. 11, device 20 includes a fluid conduit 102 with a port 104 that receives fluid and a port 106 that introduces fluid into inlet port 30. As will be recognized by those of skill in the art, conduits 102 may be a standard "Y" type connector well known in the art. One branch of conduit 102 includes port 104, whereas the other branch includes port 106. A further port 108 is connected to tube or "dummy line" 110, discussed in greater detail below.

A similar arrangement is provided at outlet port 32. As shown in FIG. 11, a fluid conduit 112, such as, but not limited to a branched "Y" is provided. One branch 114 of conduit 112 communicates with outlet port 32. Branch 116 of conduit 112 communicates with tube 118, which ultimately communicates with tube 18 and the receiving container 14. A port 120 of conduit 112 is connected to tube or "dummy line" 122.

In accordance with the present invention, it may be desired or even necessary to occasionally vent air from receiving container 14. Typically, this is achieved by "burping" air from receiving container 14 through a line in system 10. In many of the embodiments, this flow path is provided as bypass tube 38. In FIGS. 1A, 2A and 11, a bypass tube 38 defines a flow path that provides a vent for air from system 10, and specifically container 14. Bypass tube 38 includes a one-way check valve 40. Line 38 with valve 40 allows air to be vented from receiving container 14.

Where bypass tube 38 is included, an additional branched flow conduit may also be provided as shown in FIG. 11. In one preferred embodiment, additional conduits may also be branched connectors 126 and 128. In a preferred embodiment, these branched conduits 126 and 128 are trifurcated conduits, such as, but not limited to, triple "Y" connectors of the type that will be known to those of skill in the art.

Thus, flow through the processing system 10 shown in FIG. 11 is as follows. Fluid flows from source container 12 through line 16. It enters branched conduit 126. In the preferred embodiment, branched conduit is a trifurcated conduit, as shown. One tube 129 extends from port 126A and is received by port 104 of conduit 102. At this point, it should be noted that tube 110, may be a "dummy line" which is sealed or flow therethrough otherwise restricted. Accordingly, flow through bifurcated conduit 102 is necessarily directed through port 106, through which it enters device 20. This branched conduit effectively reverses the direction of flow by 180°.

Once the fluid has passed through the device, where it contacts removing medium 60, it enters outlet 32. Flow exits the device 20 through port 32 and enters conduit 112 through port 114. As with fluid conduit 102, tube 122 is a "dummy line" that is sealed or flow therethrough is otherwise restricted. This prevents flow from entering the tube 122 and directs the flow through tube 118. Tube 118 communicates with conduit 128 and in particular port 128a. Port 128a communicates with tube 18 through which fluid is passed and collected in receiving container 14.

As shown in FIG. 11, a bypass tube 38 may also be provided. One end of bypass tube 38 communicates with port 128c of the trifurcated conduit 128, while the other end of line 38 communicates with 126c of the trifurcated conduit 126.

Alternative fluid circuits are shown in FIGS. 12-16. In FIG. 12, inlet port 30 and outlet port 32 are T-shaped ports which include openings facing both away from and toward center 36 of device 20. With this arrangement, the trifurcated conduit of FIG. 11 can be eliminated. Accordingly, as shown in FIG. 12, flow enters fluid conduit 112 and is directed to inlet port 30. The embodiment of FIG. 12 includes line 130 with a one-way check valve 40a of the type previously described. Check valve 40a, shown in FIG. 12, prevents flow from entering line 130 and outlet port 132, thereby ensuring that fluid travels through tube 129 toward inlet port 30. Fluid enters device 20 and exits through outlet port 32 where it is directed to tube 134. One end of tube 134 is attached to one branch of outlet 32, while the other end of tube 134 is attached to branched conduit 102.

Figure 13:
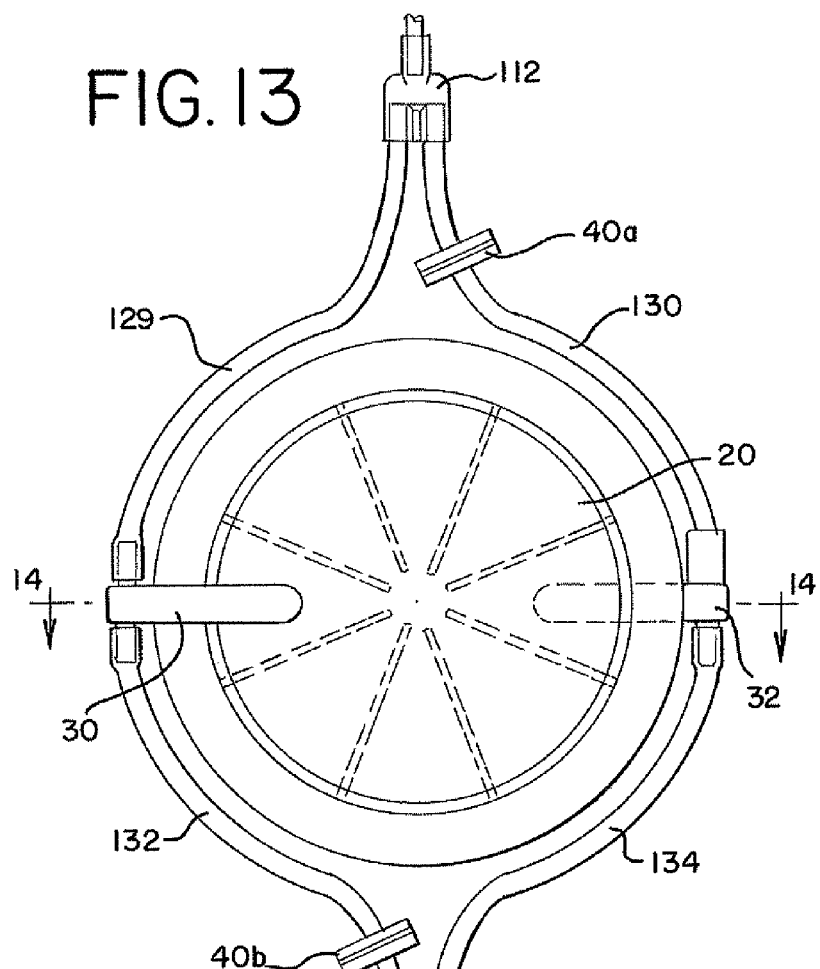
FIG. 13 is a plan view of still another embodiment of a flow-through system including a flow-through removal device.
Figure 14:
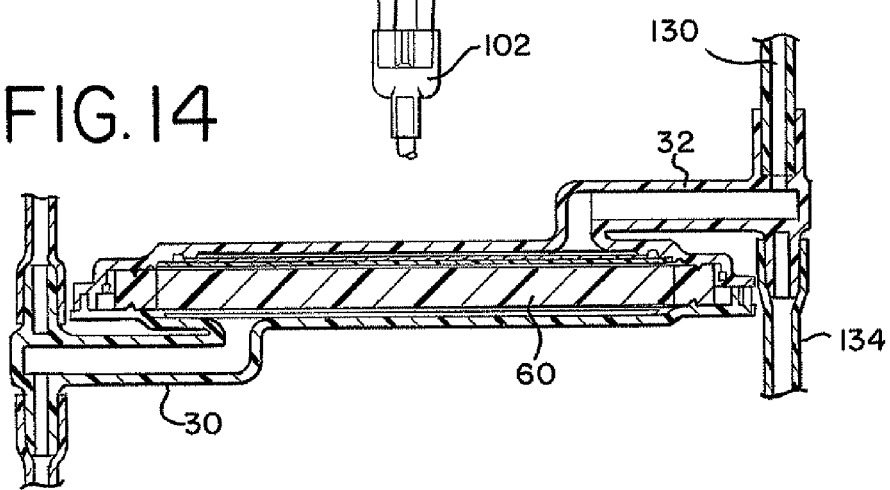
FIG. 14 is a side cross-sectional view of the system shown in FIG. 13.

A further alternative embodiment is shown in FIG. 13. This embodiment is similar in many respects to the embodiment of FIG. 12, in that it includes T-shaped ports 30 and 32. The embodiment of FIG. 13 likewise includes bifurcated conduits 112 and 102. Tubes 130 and 132 are equipped with check valves 40a and 40b. Flow enters device 20 at inlet port 30 and exits device 20 at outlet port 32.

A further alternative embodiment is shown in FIGS. 15-16. The embodiment of FIGS. 15 and 16 is similar in many respects to that shown in FIG. 11. In lieu of Y-type connectors, however, U-shaped conduits 136 and 138 may be provided for communicating with the inlet and outlet ports 30 and 32 of housing 42. The embodiment shown in FIGS. 15 and 16 may further include bifurcated conduits 140 and 142, which conduits are in flow communication with line 16 providing a flow path from source container 12 and line 18 leading to receiving container 14. As shown in FIG. 15, conduit 142 communicates fluid from tube 16 through tube 144. Tube 144 is connected to U-shaped flow conduit 136 attached to inlet port 30 of device 20. Fluid exits device 20 through outlet port 32, as previously described, and is diverted by U-shaped conduit 138 to tube 146. Tube 146, in turn, communicates with Y-type conduit 140 and ultimately with receiving container 14. A bypass line 38 may also be provided (for reasons previously described), including one-way check valve 40.

Turning now to FIGS. 25 and 26, there is shown another alternative embodiment of a removal device embodying the present invention. In this embodiment, inlet port 30 is located between center 36 and source container 12, and outlet 32 is located between center 36 and receiving container 14. Inlet port 30 and outlet 32 are in flow communication with internal channels 190 and 192, respectively.

The tubing configurations described above assist in maintaining housing 42 in a substantially vertical orientation. As described above, this allows for substantially uniform and complete exposure of the biological fluid to the removal media 60.

Figure 17:
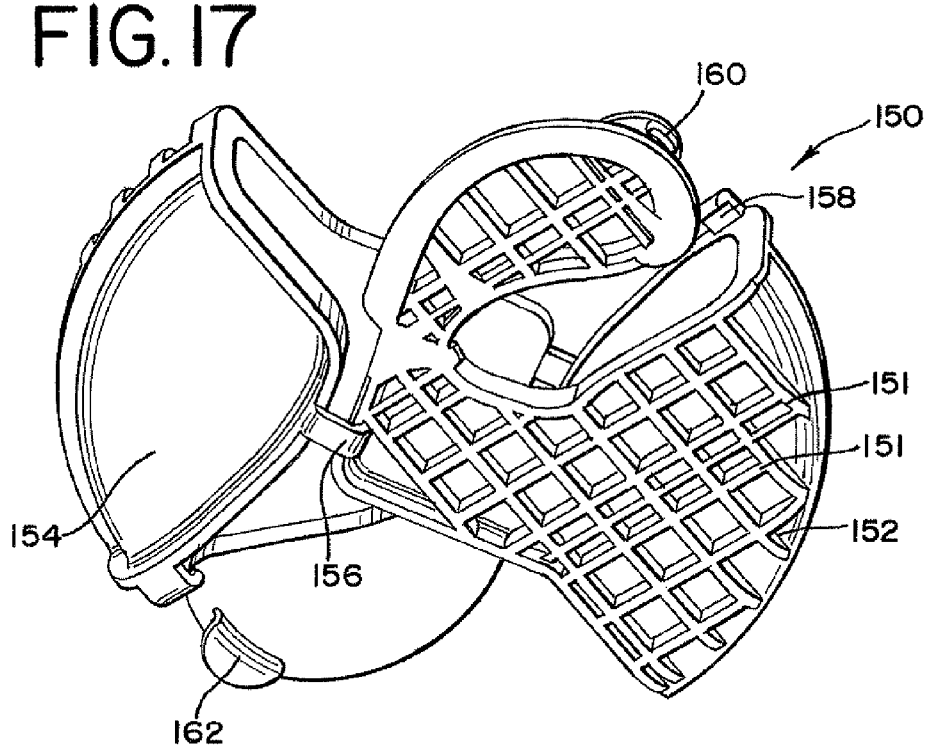
FIG. 17 is a perspective view of a holder for supporting a flow-through removal device embodying the present invention.
Figure 18:
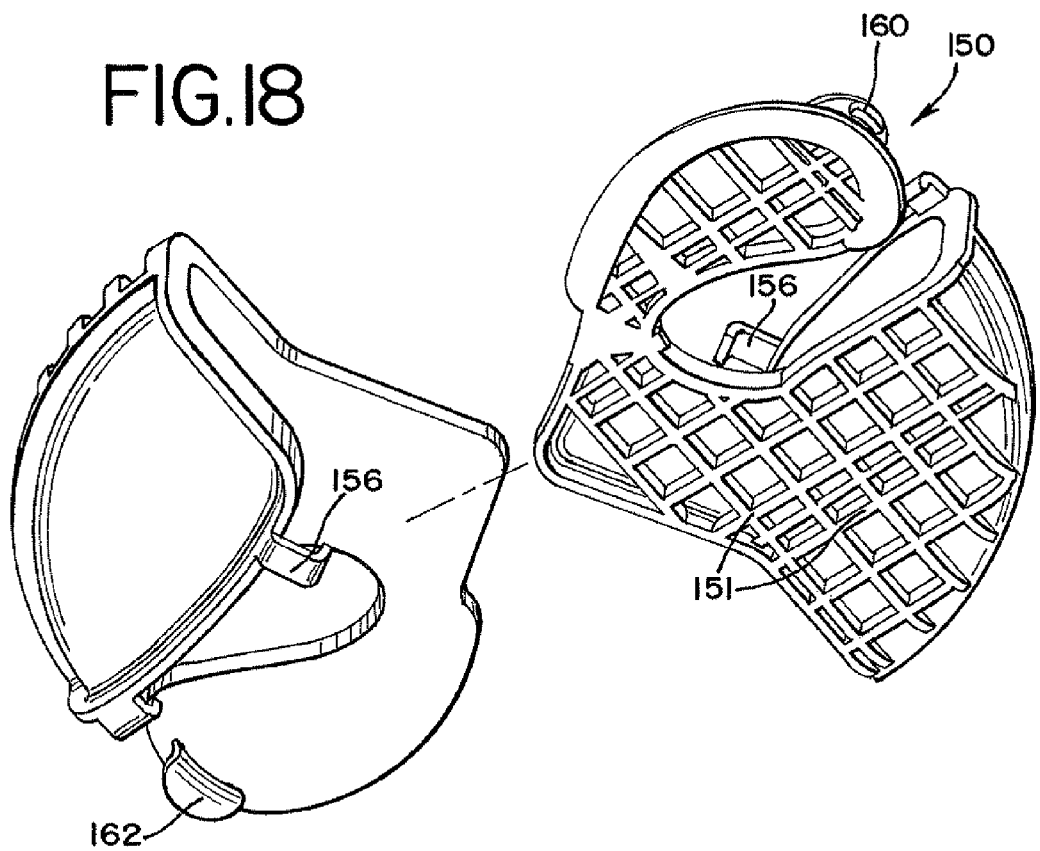
FIG. 18 is an exploded view of the holder of FIG. 17.

Finally, shown in FIGS. 17-24 are additional ways of organizing the fluid circuit of a fluid processing set 10 of the present invention, and substantially maintaining the vertical orientation of device 20. Shown in FIGS. 17-21 is an external holder used for holding device 20. As shown in FIG. 17, holder 150 may be made of two separable parts 152 and 154 that are clipped or otherwise joined together. Holder 150 may be made of a suitable plastic material and injection molded. Holder 150 may include stiffening ribs 151 to provide additional stiffness. As shown in FIGS. 17 and 18, holder 150 may include tube guiding clips 158, 160, 162 into which tubes from processing set 10 may be press-fit. As shown in FIG. 21, clips 160 (and 162) define a channel which receives tubing. In addition, clips 160 and 162 also assist in guiding tubes 16 and 18 through a 180°0 turn without kinking. As described above, turning the tubing approximately 180° allows entry of fluid at the "bottom" of device 20 and exit of fluid through the "top" of device 20.

As shown in FIG. 18, both portions 154 and 152 of holder 150 may be identical. This allows one molding tool to be used for both parts of the holder 150.

Additional means for retaining device 20 are shown in FIGS. 22-24. In these embodiments, device 20 is nested in a saddle-type holder 170. Saddle 170 may also include tube guiding clips 172 for directing tubes of the processing set in the desired configuration and direction. Also, as shown in FIGS. 22-24, to further ensure the desired vertical disposition of the device 20, hooks 180 may be provided to hold two portions of the fluid circuit in close proximity to each other. Finally, as shown in FIG. 24, the entire saddle, or holder, 170 may be attached to a vertically standing IV pole 182.

Another important objective achieved by the present invention is the ability to ensure processing time consistency from one disposable set to the next. The challenge, of course, resides in the fact that there are inherent differences in the resistance to flow from removal medium disk to removal medium disk. Applicants have discovered that flow through the system can be substantially controlled and, thus, the influence of the resistance from disk 60, substantially diminished. In particular, and as discussed in more detail below, by adjusting the length of the flow path and the internal diameters of inlet tube 16 and outlet tube 18, it is possible to provide substantially consistent processing times from one set to the next.

For example, by lengthening the flow path of the system, namely the distance from source container 12 to collection container 14 (i.e., the "head height"), the force driving flow through the system may be increased. In addition, locating device 20 further from the source container 12 and closer to receiving container 14 (as generally depicted in FIG. 1) increases the force on the fluid flowing through inlet tube 16 and entering device 20 at inlet port 30 during priming.

Thus, for example, the length of tube 16 may be approximately 1.5 to 8 times as long as tube 18. In one specific, non-limiting example, the length of tube 16 may be approximately 26 inches and the length of tube 18, approximately 3½ inches.

It has also been discovered that additional control over the flow rate can be achieved by adjusting the diameter of the flow path(s). For example, by narrowing the internal diameter of inlet tube 16 (as compared to the diameter found in standard sized tubings used in blood processing and the medical field, generally), together with the lengthening of the overall "head height," as discussed above, the resulting flow rate is sufficient to substantially reduce the effect of the inherent resistance of the removal medium or disk. Thus, flow can be better controlled and remain relatively insensitive to the resistance provided by the disk.

For example, inlet tubing, disk and outlet tubing form a hydraulic circuit that can be described as resistances in series (R1 for inlet tubing, R2 for disk and R3 for outlet tubing and Rr describing additional resistances from connectors (such as Y-sites, diameter changes and other connections). Thus, total resistance in the fluid circuit is the sum of these individual resistances. The driver for the flow is head-height as described above.

It is known that disk manufacturing will generate variability in R2 resistance. If, R2 is the dominant resistor in the circuit, the variations in its magnitude will cause significant variations in flow rate and ultimately processing time. Thus, the impact of disk manufacturing variability can be minimized by making another component in the circuit, specifically inlet tubing R1, the dominant resistor. Since tubing ID and length manufacturing tolerances are controllable to a higher degree compared to disk manufacturing, inherent variations in R1 are expected to be significantly smaller in magnitude compared to R2 variances. Inlet tube resistance is primarily defined by the internal diameter of the tube and secondarily by the length for the laminar flow regime of interest (Reynolds number 100-1000). Thus, the internal diameter (of tube 16) is the primary parameter to be changed.

Selection of the inlet tubing compared to outlet tubing as the primary restrictor is also driven by relative tube length considerations. The rationale of having longer tube length on the inlet side of the processing set as compared to outlet side has been discussed above. By selecting R1 as the dominant resistor, added benefit from tube length is gained as well.

Thus, whereas standard tubing used in blood processing typically has an internal diameter of approximately 0.118 inches, to provide the benefits described above, the internal diameter of tube 16 must be less than the standard and, more preferably, substantially less than the above-identified diameter. In one preferred, non-limiting example, the internal diameter of the inlet tube 16 may be anywhere between 0.025 and 0.09 inches. Even more preferably, the internal diameter of the tubing may be approximately 0.057±0.03 inches.

Further improvement in the processing time and flow consistency can also be achieved by altering the internal diameter of outlet tubes that are in flow communication with outlet 30. In one embodiment, the internal diameter of the outlet tube 18 (and/or tube 118 in FIG. 11, and/or tube segment 146 in FIG. 16) may be between approximately 0.04 inches and 0.120 inches. More preferably, the internal diameter of tube in flow communication with outlet may be approximately 0.080±0.03 inches. Narrowing the internal diameter of these outlet tubes (as compared to the internal diameter found in standard size tubing) assists in driving out air bubbles that may otherwise accumulate and restrict flow.

The present invention has been described in the context of its preferred embodiments. It will be understood, however, that the present invention is not limited to the embodiments described, and that further improvements and modifications may be made without departing from the scope of the present invention which is set forth in the appended claims.

What is claimed:

1. A flow-through device for removing selected compounds from a liquid comprising:
   a housing including a pair of rigid side walls welded together near their peripheries to provide a peripheral end wall, said side walls and end wall defining a chamber, wherein one of said side walls comprises an inlet port in flow communication with said chamber and the other of said side walls comprises an outlet port in flow communication with said chamber, and wherein one of said side walls includes a continuous tongue near the periphery of said wall and the other of said side walls comprises a continuous groove at or near the periphery of said other side wall for receiving said tongue, wherein said groove is defined by radial inner and outer walls, at least one of said walls including a shoulder extending therefrom, whereby said shoulder is disposed relative to said tongue such that during assembly, said tongue initially contacts said shoulder; said housing further including at least one injection port in flow communication with said chamber, a compound removal medium comprising a sintered medium comprising a particulate of a sorbent composition and a polymeric binder, said compound removal medium located within said chamber between said walls, said compound removal medium including a peripheral end surface terminating interior to said peripheral end wall of said housing thereby defining a gap between said peripheral end surface and said peripheral end wall, wherein said compound removal medium peripheral end is in contact with a liquid impermeable barrier, said liquid impermeable barrier further comprising an injectable material and wherein said material is injected through said injection port, said material substantially filling said gap between said peripheral end surface of said compound removal medium and said peripheral end wall of said housing; and a gripping member extending from at least one of said side walls and located radially interior to said tongue and groove and extending a sufficient distance from said side wall such that at least one gripping member contacts said removal medium, a sheet of filter material disposed between said compound removal medium and said housing side wall including said outlet port, wherein said outlet housing side wall comprises a nesting surface for supporting said filter and wherein the peripheral portion of said filter material is held at said nesting surface, wherein said filter material is permeable to said liquid but substantially impermeable to said particulate.

2. The flow through device of claim 1 wherein at least one of said inner housing surfaces includes a gripping member extending from said surface into said chamber and gripping said removal medium, said member being integrally spaced from said peripheral end wall of said housing.

3. Apparatus of claim 2 wherein said removal medium is partially compressed by said gripping member.

4. The flow-through device of claim 2 wherein said housing comprises a gripping member extending from the inner surface of one of said pair of walls and a gripping member extending from the inner surface of the other pair of walls.

5. The flow-through device of claim 2 wherein said member terminates in a substantially pointed tip.

6. Apparatus of claim 1 wherein said housing is made of a material that is suitable for sonic welding.

7. Apparatus of claim 6 wherein said housing is made of polymethyl methacrylate.

8. Apparatus of claim 1 wherein said filter material is adhered to said surface by sonic welding.

9. Apparatus of claim 1 wherein at least one of said side walls comprises a plurality of inwardly extending ribs on the inner surface thereof.

10. Apparatus of claim 9 comprising a center, wherein said ribs extend radially from a point adjacent to said center point to a point adjacent to the peripheral edge of said housing.

11. Apparatus of claim 1 comprising a pair of raised ribs on said side walls and said outlet or inlet port is disposed between said ribs.

12. Apparatus of claim 1 wherein the end of said tongue is rounded.

13. The flow-through device of claim 1;
wherein said housing further comprises an upper end, a lower end, and a center between said upper and lower ends; and
wherein the inlet port on one of said side walls is located between said center and said lower end of said housing, and the outlet port on the other of said side walls is located between said center and said upper end of said housing and diametrically opposite to said inlet port.

14. Device of claim 13 comprising a fluid source end and a fluid receiving end, wherein said outlet port is located nearer said fluid source end than said inlet.

15. Device of claim 13 wherein said housing inlet and said outlet are spaced 90° from the central vertical axis of said housing.

16. The flow-through device of claim 1 wherein said injectable material is selected from the group consisting of epoxies, RTV sealants, hot melts, polyurethane, silicones, waxes and plastics.

17. The flow through device of claim 1 wherein the compound removal medium comprises a disk of a sintered polymer.

* * * * *